United States Patent
Wang et al.

(10) Patent No.: US 11,655,292 B2
(45) Date of Patent: May 23, 2023

(54) ANTI-HUMAN NGF ANTIBODIES AND METHODS USING SAME

(71) Applicant: AMPSOURCE BIOPHARMA SHANGHAI INC., Shanghai (CN)

(72) Inventors: Zhu Wang, Shanghai (CN); Yongjuan Gao, Shanghai (CN); Si Chen, Shanghai (CN); Cecily Rou-Yun Sun, Shanghai (CN); Yuncheng Zheng, Shanghai (CN); Bill Nai-Chau Sun, Shanghai (CN); Qiang Li, Shanghai (CN)

(73) Assignee: AMPSOURCE BIOPHARMA SHANGHAI INC., Shanghai (CN)

( * ) Notice: Subject to any disclaimer, the term of this patent is extended or adjusted under 35 U.S.C. 154(b) by 0 days.

(21) Appl. No.: 16/909,881

(22) Filed: Jun. 23, 2020

(65) Prior Publication Data
US 2021/0395354 A1    Dec. 23, 2021

(51) Int. Cl.
*C07K 16/22*    (2006.01)
*A61K 38/18*    (2006.01)

(52) U.S. Cl.
CPC ............ *C07K 16/22* (2013.01); *A61K 38/185* (2013.01); *C07K 2317/24* (2013.01); *C07K 2317/565* (2013.01); *C07K 2317/92* (2013.01)

(58) Field of Classification Search
CPC ............ C07K 16/18; C07K 16/22; C07K 2317/565; C07K 2317/92; A61K 38/185
See application file for complete search history.

(56) References Cited

U.S. PATENT DOCUMENTS

| | | |
|---|---|---|
| 8,198,410 B2 | 6/2012 | Wild, Jr. et al. |
| 9,505,829 B2 | 11/2016 | Lacy et al. |
| 2009/0041717 A1 | 2/2009 | MacDonald et al. |
| 2009/0208490 A1 | 8/2009 | Pavone et al. |
| 2010/0034818 A1 | 2/2010 | Wild, Jr. et al. |
| 2010/0278839 A1 | 11/2010 | Powell et al. |
| 2017/0260264 A1 | 9/2017 | Powell et al. |

FOREIGN PATENT DOCUMENTS

CN    109929035 A    6/2019

OTHER PUBLICATIONS

Miller, R.E., et al., Nerve Growth Factor (NGF) Blockade for the Management of Osteoarthritis Pain: What Can We Learn From Clinical Trials and Preclinical Models?; Curr Opin Rheumatol. Jan. 2017; 29(1), 110-118.

*Primary Examiner* — Olga N Chernyshev
(74) *Attorney, Agent, or Firm* — Honigman LLP; Thomas A. Wootton, Esq.; Jonathan P. O'Brien

(57) ABSTRACT

The invention provides an antibody and/or an antigen binding fragment that binds to NGF, and the amino acid sequences of the heavy chain and light chain variable regions of the antibody. The NGF antibody and/or its antigen binding fragment provided by the invention has high affinity for NGF and can effectively block the binding between NGF receptor and NGF. This antibody and/or its antigen binding fragment can inhibit the binding activity of NGF and its receptor in vitro, and is suitable for the treatment of pain diseases which are related to the haughty expression or increased expression of NGF.

Figure 1:
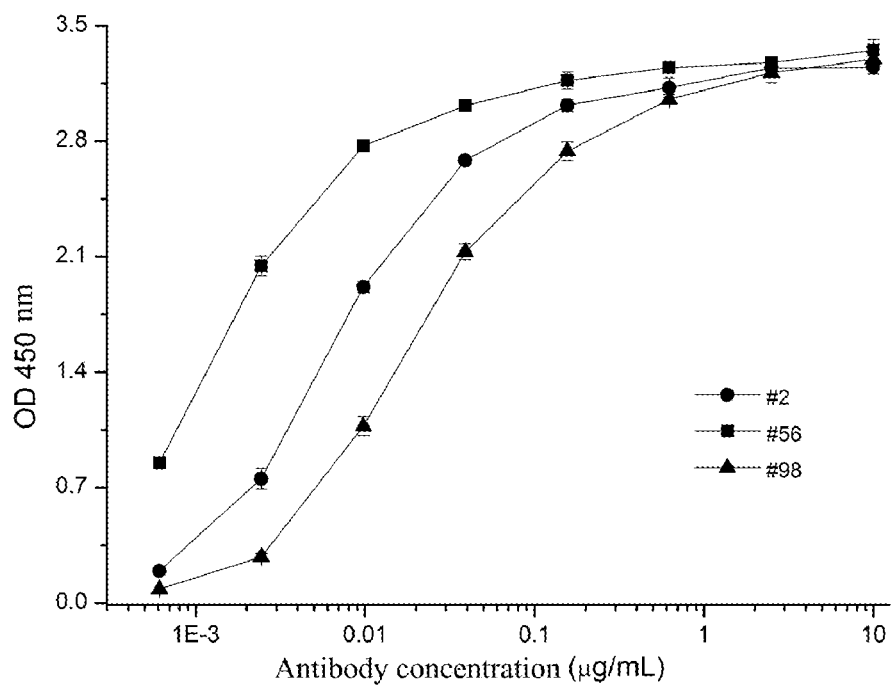

8 Claims, 8 Drawing Sheets
Specification includes a Sequence Listing.

| Inventor(s): | Zhu WANG, et al. | Art Unit: | 1649 |
|---|---|---|---|
| Application No.: | 16/909,881 | Confirmation No.: | 6184 |
| Filing Date: | June 23, 2020 | Examiner: | Olga N. Chernyshev |
| Page: | 6 of 11 | Attorney Docket No.: | 262790-468320 |

REPLACEMENT DRAWINGS

In the following order: 3-1, 3-2, 4-1 and 4-2

```
                    FR-H1                  CDR-H1      FR-H2
    #56-V_H   QVQLKESGPGLVAPSQSLSITCTVS   GFSLTGYG   VNWVRQP
    AB5C2-V_H  ----Q-------K--ET--L-----   --------   -------
    AB5C3-V_H  ----Q-------K--ET--L-----   --------   WG-I---
    AB5C4-V_H  ----Q-------K--ET--L-----   --------   WG-----
    AB5C5-V_H  ----Q-------K--ET--L-----   --------   WG-----
    AB5C6-V_H  --------------ET---------   --------   -------

CDR-H2                  FR-H3
    #56-V_H   PGKGLEWLGM   IWADGDT   DYNSALKSRLSISKDNSKSQVFL
    AB5C2-V_H  ----------   -------   ----------VT----T--N-FS-
    AB5C3-V_H  -------I-S   -------   Y--PS----VT--V-T--N-FS-
    AB5C4-V_H  -------I-S   -------   Y--PS----VT--V-T--N-FS-
    AB5C5-V_H  ---------S   -------   Y--PS----VT--V-T--N-FS-
    AB5C6-V_H  ----------   -------   ------------T----------

CDR-H3            FR-H4
    #56-V_H   KVNNLQTDDTARYYC   ARDSYYYGYNFFDV   WGAGTTVTVSS   (SEQ ID NO: 13)
    AB5C2-V_H  -LSSVTAA-------   --------------   -----------   (SEQ ID NO: 17)
    AB5C3-V_H  -LSSVTAA---V---   --------------   --Q--M-----   (SEQ ID NO: 19)
    AB5C4-V_H  -LSSVTAA---V---   --------------   --Q--M-----   (SEQ ID NO: 21)
    AB5C5-V_H  -LSSVTAA---V---   --------------   --Q--M-----   (SEQ ID NO: 23)
    AB5C6-V_H  ---------------   --------------   -----------   (SEQ ID NO: 25)
```

Figure 3-1

| Inventor(s): | Zhu WANG, et al. | Art Unit: | 1649 |
| --- | --- | --- | --- |
| Application No.: | 16/909,881 | Confirmation No.: | 6184 |
| Filing Date: | June 23, 2020 | Examiner: | Olga N. Chernyshev |
| Page: | 7 of 11 | Attorney Docket No.: | 262790-468320 |

```
              FR-L1                          CDR-L1    FR-L2
#56-VL   DIQMTQTTSSLSASLGDRVTISCRAS         QDISNY    LNWYQQKP
AB5C2-VL ------SP-------V-------T-----      ------    --------
AB5C3-VL ------SP-------V-------T-Q--       ------    --------
AB5C4-VL ------SP-------V-------T-Q--       ------    --------
AB5C5-VL ------SP-------V-------T-Q--       ------    --------
AB5C6-VL ------SP-------V------------       ------    --------

CDR-L2           FR-L3
#56-VL   EGTLKLLIY   YTS   RLHSGVPSRFSGSGSGTDYSLTISSLEQ
AB5C2-VL GKAP-----   ---   ---------------------FTF----QP
AB5C3-VL GKAP-----   ---   N-ET-----------------FTF----QP
AB5C4-VL GKAP-----   ---   N-E------------------FTF----QP
AB5C5-VL GKAP-----   ---   N-E------------------FTF----QP
AB5C6-VL ---------   ---   --------------------------Q--

CDR-L3        FR-L4
#56-VL   EDIATYFC   QQGNTLPRT   FGGGTKLEIK   (SEQ ID NO: 14)
AB5C2-VL --------   ---------   ------V---   (SEQ ID NO: 18)
AB5C3-VL ------Y-   ---------   ------V---   (SEQ ID NO: 20)
AB5C4-VL ------Y-   ---------   ------V---   (SEQ ID NO: 22)
AB5C5-VL --------   ---------   ------V---   (SEQ ID NO: 24)
AB5C6-VL --------   ---------   ----------   (SEQ ID NO: 26)
```

Figure 3-2

| | FR-H1 | CDR-H1 | FR-H2 | |
|---|---|---|---|---|
| #2-V_H | QVQLQQSGPELARPGASVKLSCKAS | GYTPTDYW | MQWVKQR | |
| AB5D2-V_H | ----V---A-VKK------V---- | -------- | ------- | |
| AB5D3-V_H | ----V---A-VKK------V---- | -------- | -H--R-A | |
| AB5D4-V_H | ----V---A-VKK------V---- | -------- | -H----A | |
| AB5D5-V_H | ----V---A-VKK------V---- | -------- | -H----A | |
| AB5D6-V_H | ----------V-K----------- | -------- | ------- | |

| | | CDR-H2 | FR-H3 | |
|---|---|---|---|---|
| #2-V_H | PGQGLEWIGT | IYPGDGYT | RYIQKFKGRATLTADKSSSTAY | |
| AB5D2-V_H | ---------- | -------- | -----------V-M-R-T-T--V- | |
| AB5D3-V_H | -------M-I | -------- | S-A---Q--V-M-R-T-T--V- | |
| AB5D4-V_H | -------M-I | -------- | S-A---Q--V-M-R-T-T--V- | |
| AB5D5-V_H | -------M-I | -------- | S-----Q--V-M-R-T-T--V- | |
| AB5D6-V_H | ---------- | -------- | ---------------------T---- | |

| | | CDR-H3 | FR-H4 | |
|---|---|---|---|---|
| #2-V_H | MQLNSLASEDSAVYYC | ARRAAYYTMDY | WGQGTSVTVSS | (SEQ ID NO: 15) |
| AB5D2-V_H | -E-S--R--------- | ----------- | -----L----- | (SEQ ID NO: 27) |
| AB5D3-V_H | -E-S--R---T----- | ----------- | -----L----- | (SEQ ID NO: 29) |
| AB5D4-V_H | -E-S--R---T----- | ----------- | -----L----- | (SEQ ID NO: 31) |
| AB5D5-V_H | -E-S--R---T----- | ----------- | -----L----- | (SEQ ID NO: 33) |
| AB5D6-V_H | -E-------------- | ----------- | ----------- | (SEQ ID NO: 35) |

Figure 4-1

| | | FR-L1 | CDR-L1 | FR-L2 |
|---|---|---|---|---|
| #2-V$_L$ | | DIVMTQSHKFMSTSVGDRVSITCKAS | QDVNTA | VAWYQQKP |
| AB5D2-V$_L$ | | --Q-----PSSL-A-------T------ | ------ | -------- |
| AB5D3-V$_L$ | | --Q-----PSSL-A-------T---R-- | ------ | L------- |
| AB5D4-V$_L$ | | --Q-----PSSL-A-------T---R-- | ------ | L------- |
| AB5D5-V$_L$ | | --Q-----PSSL-A-------T---R-- | ------ | L------- |
| AB5D6-V$_L$ | | --------------------T------- | ------ | -------- |

| | CDR-L2 | | FR-L3 |
|---|---|---|---|
| #2-V$_L$ | GQSPKLLIY | WAS | TRHTGVPDRFTGSGSGTDYILTISSVQA |
| AB5D2-V$_L$ | -KA------ | --- | --------------------T-----L-P |
| AB5D3-V$_L$ | -KA----L- | --- | RLES---S--S---------T-----L-P |
| AB5D4-V$_L$ | -KA----L- | --- | RLE----S--S---------T-----L-P |
| AB5D5-V$_L$ | -KA----L- | --- | RLE----S--S---------T-----L-P |
| AB5D6-V$_L$ | --------- | --- | ----------S----------------- |

| | | CDR-L3 | FR-L4 | |
|---|---|---|---|---|
| #2-V$_L$ | EDLALYYC | QQHYSSPWT | FGGGTKLEIT | (SEQ ID NO: 16) |
| AB5D2-V$_L$ | -------- | --------- | ------V--- | (SEQ ID NO: 28) |
| AB5D3-V$_L$ | --F-T--- | --------- | ------V--- | (SEQ ID NO: 30) |
| AB5D4-V$_L$ | --F-T--- | --------- | ------V--- | (SEQ ID NO: 32) |
| AB5D5-V$_L$ | ----T--- | --------- | ------V--- | (SEQ ID NO: 34) |
| AB5D6-V$_L$ | -------- | --------- | ---------- | (SEQ ID NO: 36) |

Figure 4-2

SEQUENCE LISTING

```
<160> NUMBER OF SEQ ID NOS: 63

<210> SEQ ID NO 1
<211> LENGTH: 8
<212> TYPE: PRT
<213> ORGANISM: Artificial sequence
<220> FEATURE:
<223> OTHER INFORMATION: CDR-H1 of #56

<400> SEQUENCE: 1
```

```
Gly Phe Ser Leu Thr Gly Tyr Gly
1               5

<210> SEQ ID NO 2
<211> LENGTH: 8
<212> TYPE: PRT
<213> ORGANISM: Artificial sequence
<220> FEATURE:
<223> OTHER INFORMATION: CDR-H1 of #2

<400> SEQUENCE: 2

Gly Tyr Thr Phe Thr Asp Tyr Trp
1               5

<210> SEQ ID NO 3
<211> LENGTH: 7
<212> TYPE: PRT
<213> ORGANISM: Artificial sequence
<220> FEATURE:
<223> OTHER INFORMATION: CDR-H2 of #56

<400> SEQUENCE: 3

Ile Trp Ala Asp Gly Asp Thr
1               5

<210> SEQ ID NO 4
<211> LENGTH: 8
<212> TYPE: PRT
<213> ORGANISM: Artificial sequence
<220> FEATURE:
<223> OTHER INFORMATION: CDR-H2 of #2

<400> SEQUENCE: 4

Ile Tyr Pro Gly Asp Gly Tyr Thr
1               5

<210> SEQ ID NO 5
<211> LENGTH: 14
<212> TYPE: PRT
<213> ORGANISM: Artificial sequence
<220> FEATURE:
<223> OTHER INFORMATION: CDR-H3 of #56

<400> SEQUENCE: 5

Ala Arg Asp Ser Tyr Tyr Tyr Gly Tyr Asn Phe Phe Asp Val
1               5                   10

<210> SEQ ID NO 6
<211> LENGTH: 11
<212> TYPE: PRT
<213> ORGANISM: Artificial sequence
<220> FEATURE:
<223> OTHER INFORMATION: CDR-H3 of #2

<400> SEQUENCE: 6

Ala Arg Arg Ala Ala Tyr Tyr Thr Met Asp Tyr
1               5                   10

<210> SEQ ID NO 7
<211> LENGTH: 6
<212> TYPE: PRT
<213> ORGANISM: Artificial sequence
<220> FEATURE:
<223> OTHER INFORMATION: CDR-L1 of #56
```

```
<400> SEQUENCE: 7

Gln Asp Ile Ser Asn Tyr
1               5

<210> SEQ ID NO 8
<211> LENGTH: 6
<212> TYPE: PRT
<213> ORGANISM: Artificial sequence
<220> FEATURE:
<223> OTHER INFORMATION: CDR-L1 of #2

<400> SEQUENCE: 8

Gln Asp Val Asn Thr Ala
1               5

<210> SEQ ID NO 9

<400> SEQUENCE: 9

000

<210> SEQ ID NO 10

<400> SEQUENCE: 10

000

<210> SEQ ID NO 11
<211> LENGTH: 9
<212> TYPE: PRT
<213> ORGANISM: Artificial sequence
<220> FEATURE:
<223> OTHER INFORMATION: CDR-L3 of #56

<400> SEQUENCE: 11

Gln Gln Gly Asn Thr Leu Pro Arg Thr
1               5

<210> SEQ ID NO 12
<211> LENGTH: 9
<212> TYPE: PRT
<213> ORGANISM: Artificial sequence
<220> FEATURE:
<223> OTHER INFORMATION: CDR-L3 of #2

<400> SEQUENCE: 12

Gln Gln His Tyr Ser Ser Pro Trp Thr
1               5

<210> SEQ ID NO 13
<211> LENGTH: 120
<212> TYPE: PRT
<213> ORGANISM: Artificial sequence
<220> FEATURE:
<223> OTHER INFORMATION: Amino acid sequence of heavy chain variable
      region of #56

<400> SEQUENCE: 13

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45
```

```
Gly Met Ile Trp Ala Asp Gly Asp Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Val Asn Asn Leu Gln Thr Asp Asp Thr Ala Arg Tyr Tyr Cys Ala
                85                  90                  95

Arg Asp Ser Tyr Tyr Tyr Gly Tyr Asn Phe Phe Asp Val Trp Gly Ala
            100                 105                 110

Gly Thr Thr Val Thr Val Ser Ser
            115                 120

<210> SEQ ID NO 14
<211> LENGTH: 107
<212> TYPE: PRT
<213> ORGANISM: Artificial sequence
<220> FEATURE:
<223> OTHER INFORMATION: Amino acid sequence of light chain variable
      region of #56

<400> SEQUENCE: 14

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Lys Pro Glu Gly Thr Leu Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Ser Leu Glu Gln
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Leu Glu Ile Lys
            100                 105

<210> SEQ ID NO 15
<211> LENGTH: 118
<212> TYPE: PRT
<213> ORGANISM: Artificial sequence
<220> FEATURE:
<223> OTHER INFORMATION: Amino acid sequence of heavy chain variable
      region of #2

<400> SEQUENCE: 15

Gln Val Gln Leu Gln Gln Ser Gly Pro Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Tyr Thr Arg Tyr Ile Gln Lys Phe
50                  55                  60

Lys Gly Arg Ala Thr Leu Thr Ala Asp Lys Ser Ser Thr Ala Tyr
65                  70                  75                  80

Met Gln Leu Asn Ser Leu Ala Ser Glu Asp Ser Ala Val Tyr Tyr Cys
                85                  90                  95

Ala Arg Arg Ala Ala Tyr Tyr Thr Met Asp Tyr Trp Gly Gln Gly Thr
            100                 105                 110
```

Ser Val Thr Val Ser Ser
         115

<210> SEQ ID NO 16
<211> LENGTH: 107
<212> TYPE: PRT
<213> ORGANISM: Artificial sequence
<220> FEATURE:
<223> OTHER INFORMATION: Amino acid sequence of light chain variable
      region of #2

<400> SEQUENCE: 16

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Ile Leu Thr Ile Ser Ser Val Gln Ala
65                  70                  75                  80

Glu Asp Leu Ala Leu Tyr Tyr Cys Gln Gln His Tyr Ser Ser Pro Trp
                85                  90                  95

Thr Phe Gly Gly Gly Thr Lys Leu Glu Ile Thr
            100                 105

<210> SEQ ID NO 17
<211> LENGTH: 120
<212> TYPE: PRT
<213> ORGANISM: Artificial sequence
<220> FEATURE:
<223> OTHER INFORMATION: Amino acid sequence of heavy chain variable
      region of AB5C2 humanized antibody

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Ala Asp Gly Asp Thr Asp Tyr Asn Ser Ala Leu Lys
50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Arg Tyr Tyr Cys Ala
                85                  90                  95

Arg Asp Ser Tyr Tyr Tyr Gly Tyr Asn Phe Phe Asp Val Trp Gly Ala
            100                 105                 110

Gly Thr Thr Val Thr Val Ser Ser
        115                 120

<210> SEQ ID NO 18
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5C2

```
<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Val Glu Ile Lys
            100                 105

<210> SEQ ID NO 19
<211> LENGTH: 120
<212> TYPE: PRT
<213> ORGANISM: Artificial sequence
<220> FEATURE:
<223> OTHER INFORMATION: Amino acid sequence of heavy chain variable
      region of humanized antibody AB5C3

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
                20                  25                  30

Gly Trp Gly Trp Ile Arg Gln Pro Pro Gly Lys Gly Leu Glu Trp Ile
            35                  40                  45

Gly Ser Ile Trp Ala Asp Gly Asp Thr Tyr Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Tyr Tyr Tyr Gly Tyr Asn Phe Phe Asp Val Trp Gly Gln
            100                 105                 110

Gly Thr Met Val Thr Val Ser Ser
            115                 120

<210> SEQ ID NO 20
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5C3

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45
```

```
Tyr Tyr Thr Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Arg
                 85                  90                  95

Thr Phe Gly Gly Gly Thr Lys Val Glu Ile Lys
            100                 105
```

<210> SEQ ID NO 21
<211> LENGTH: 120
<212> TYPE: PRT
<213> ORGANISM: Artificial sequence
<220> FEATURE:
<223> OTHER INFORMATION: Amino acid sequence of heavy chain variable
      region of AB5C4 humanized antibody

<400> SEQUENCE: 21

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Gly Tyr
             20                  25                  30

Gly Trp Gly Trp Val Arg Gln Pro Pro Gly Lys Gly Leu Glu Trp Ile
         35                  40                  45

Gly Ser Ile Trp Ala Asp Gly Asp Thr Tyr Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Ser Tyr Tyr Tyr Gly Tyr Asn Phe Phe Asp Val Trp Gly Gln
            100                 105                 110

Gly Thr Met Val Thr Val Ser Ser
        115                 120
```

<210> SEQ ID NO 22
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5C4

<400> SEQUENCE: 22

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Asn Leu Glu Ser Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Arg
                 85                  90                  95

Thr Phe Gly Gly Gly Thr Lys Val Glu Ile Lys
            100                 105
```

<210> SEQ ID NO 23
<211> LENGTH: 120
<212> TYPE: PRT
<213> ORGANISM: Artificial sequence
<220> FEATURE:
<223> OTHER INFORMATION: Amino acid sequence of heavy chain variable
      region of humanized antibody AB5C5

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Trp Gly Trp Val Arg Gln Pro Pro Gly Lys Gly Leu Glu Trp Leu
        35                  40                  45

Gly Ser Ile Trp Ala Asp Gly Asp Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Tyr Tyr Tyr Gly Tyr Asn Phe Phe Asp Val Trp Gly Gln
            100                 105                 110

Gly Thr Met Val Thr Val Ser Ser
        115                 120

<210> SEQ ID NO 24
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5C5

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu Glu Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Val Glu Ile Lys
            100                 105

<210> SEQ ID NO 25
<211> LENGTH: 120
<212> TYPE: PRT
<213> ORGANISM: Artificial sequence
<220> FEATURE:
<223> OTHER INFORMATION: Amino acid sequence of heavy chain variable
      region of humanized antibody AB5C6

```
<400> SEQUENCE: 25

Gln Val Gln Leu Lys Glu Ser Gly Pro Gly Leu Val Ala Pro Ser Glu
1               5                   10                  15

Thr Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Ala Asp Gly Asp Thr Asp Tyr Asn Ser Ala Leu Lys
    50                  55                  60

Ser Arg Leu Thr Ile Ser Lys Asp Asn Ser Lys Ser Gln Val Phe Leu
65                  70                  75                  80

Lys Val Asn Asn Leu Gln Thr Asp Asp Thr Ala Arg Tyr Tyr Cys Ala
                85                  90                  95

Arg Asp Ser Tyr Tyr Tyr Gly Tyr Asn Phe Phe Asp Val Trp Gly Ala
                100                 105                 110

Gly Thr Thr Val Thr Val Ser Ser
            115                 120

<210> SEQ ID NO 26
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5C6

<400> SEQUENCE: 26

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Glu Gly Thr Leu Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Ser Leu Gln Gln
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Leu Glu Ile Lys
            100                 105

<210> SEQ ID NO 27
<211> LENGTH: 118
<212> TYPE: PRT
<213> ORGANISM: Artificial sequence
<220> FEATURE:
<223> OTHER INFORMATION: Amino acid sequence of heavy chain variable
      region of humanized antibody AB5D2

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45
```

Gly Thr Ile Tyr Pro Gly Asp Gly Tyr Thr Arg Tyr Ile Gln Lys Phe
            50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Ser Ala Val Tyr Tyr Cys
                 85                  90                  95

Ala Arg Arg Ala Ala Tyr Tyr Thr Met Asp Tyr Trp Gly Gln Gly Thr
             100                 105                 110

Leu Val Thr Val Ser Ser
            115

<210> SEQ ID NO 28
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5D2

<400> SEQUENCE: 28

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Trp Ala Ser Thr Arg His Thr Gly Val Pro Asp Arg Phe Thr Gly
 50                  55                  60

Ser Gly Ser Gly Thr Asp Tyr Thr Leu Thr Ile Ser Ser Leu Gln Pro
 65                  70                  75                  80

Glu Asp Leu Ala Leu Tyr Tyr Cys Gln Gln His Tyr Ser Ser Pro Trp
                 85                  90                  95

Thr Phe Gly Gly Gly Thr Lys Val Glu Ile Thr
             100                 105

<210> SEQ ID NO 29
<211> LENGTH: 118
<212> TYPE: PRT
<213> ORGANISM: Artificial sequence
<220> FEATURE:
<223> OTHER INFORMATION: Amino acid sequence of heavy chain variable
      region of humanized antibody AB5D3

<400> SEQUENCE: 29

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Trp Met His Trp Val Arg Gln Ala Pro Gly Gln Gly Leu Glu Trp Met
         35                  40                  45

Gly Ile Ile Tyr Pro Gly Asp Gly Tyr Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Arg Ala Ala Tyr Tyr Thr Met Asp Tyr Trp Gly Gln Gly Thr
             100                 105                 110

```
Leu Val Thr Val Ser Ser
        115

<210> SEQ ID NO 30
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5D3

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Leu Ala Trp Tyr Gln Gln Lys Pro Gly Lys Ala Pro Lys Leu Leu Leu
        35                  40                  45

Tyr Trp Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Ser Ser Pro Trp
                85                  90                  95

Thr Phe Gly Gly Gly Thr Lys Val Glu Ile Thr
            100                 105

<210> SEQ ID NO 31
<211> LENGTH: 118
<212> TYPE: PRT
<213> ORGANISM: Artificial sequence
<220> FEATURE:
<223> OTHER INFORMATION: Amino acid sequence of heavy chain variable
      region of humanized antibody AB5D4

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Lys Gln Ala Pro Gly Gln Gly Leu Glu Trp Met
        35                  40                  45

Gly Ile Ile Tyr Pro Gly Asp Gly Tyr Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Ala Ala Tyr Tyr Thr Met Asp Tyr Trp Gly Gln Gly Thr
            100                 105                 110

Leu Val Thr Val Ser Ser
        115

<210> SEQ ID NO 32
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5D4
```

-continued

```
<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Leu Ala Trp Tyr Gln Gln Lys Pro Gly Lys Ala Pro Lys Leu Leu Leu
        35                  40                  45

Tyr Trp Ala Ser Arg Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Ser Ser Pro Trp
                85                  90                  95

Thr Phe Gly Gly Gly Thr Lys Val Glu Ile Thr
            100                 105

<210> SEQ ID NO 33
<211> LENGTH: 118
<212> TYPE: PRT
<213> ORGANISM: Artificial sequence
<220> FEATURE:
<223> OTHER INFORMATION: Amino acid sequence of heavy chain variable
      region of humanized antibody AB5D5

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Lys Gln Ala Pro Gly Gln Gly Leu Glu Trp Met
        35                  40                  45

Gly Ile Ile Tyr Pro Gly Asp Gly Tyr Thr Ser Tyr Ile Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Ala Ala Tyr Tyr Thr Met Asp Tyr Trp Gly Gln Gly Thr
            100                 105                 110

Leu Val Thr Val Ser Ser
        115

<210> SEQ ID NO 34
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5D5

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Leu Ala Trp Tyr Gln Gln Lys Pro Gly Lys Ala Pro Lys Leu Leu Leu
        35                  40                  45
```

```
Tyr Trp Ala Ser Arg Leu Glu Thr Gly Val Pro Ser Arg Phe Ser Gly
        50                  55                  60

Ser Gly Ser Gly Thr Asp Tyr Thr Leu Thr Ile Ser Ser Leu Gln Pro
 65                  70                  75                  80

Glu Asp Leu Ala Thr Tyr Tyr Cys Gln Gln His Tyr Ser Ser Pro Trp
                85                  90                  95

Thr Phe Gly Gly Gly Thr Lys Val Glu Ile Thr
               100                 105

<210> SEQ ID NO 35
<211> LENGTH: 118
<212> TYPE: PRT
<213> ORGANISM: Artificial sequence
<220> FEATURE:
<223> OTHER INFORMATION: Amino acid sequence of heavy chain variable
      region of humanized antibody AB5D6

<400> SEQUENCE: 35

Gln Val Gln Leu Gln Gln Ser Gly Pro Glu Val Ala Lys Pro Gly Ala
 1               5                  10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Tyr Thr Arg Tyr Ile Gln Lys Phe
        50                  55                  60

Lys Gly Arg Ala Thr Leu Thr Ala Asp Lys Ser Thr Ser Thr Ala Tyr
 65                  70                  75                  80

Met Glu Leu Asn Ser Leu Ala Ser Glu Asp Ser Ala Val Tyr Tyr Cys
                85                  90                  95

Ala Arg Arg Ala Ala Tyr Tyr Thr Met Asp Tyr Trp Gly Gln Gly Thr
            100                 105                 110

Ser Val Thr Val Ser Ser
        115

<210> SEQ ID NO 36
<211> LENGTH: 107
<212> TYPE: PRT
<213> ORGANISM: Artificial sequence
<220> FEATURE:
<223> OTHER INFORMATION: Amino acid sequence of light chain variable
      region of humanized antibody AB5D6

<400> SEQUENCE: 36

Asp Ile Val Met Thr Gln Ser His Lys Phe Met Ser Thr Ser Val Gly
 1               5                  10                  15

Asp Arg Val Thr Ile Thr Cys Lys Ala Ser Gln Asp Val Asn Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Ser Gly
        50                  55                  60

Ser Gly Ser Gly Thr Asp Tyr Ile Leu Thr Ile Ser Ser Val Gln Ala
 65                  70                  75                  80

Glu Asp Leu Ala Leu Tyr Tyr Cys Gln Gln His Tyr Ser Ser Pro Trp
                85                  90                  95

Thr Phe Gly Gly Gly Thr Lys Leu Glu Ile Thr
               100                 105
```

```
<210> SEQ ID NO 37
<211> LENGTH: 5
<212> TYPE: PRT
<213> ORGANISM: Artificial sequence
<220> FEATURE:
<223> OTHER INFORMATION: #56 CDR-H1

<400> SEQUENCE: 37

Gly Tyr Gly Val Asn
1               5

<210> SEQ ID NO 38
<211> LENGTH: 5
<212> TYPE: PRT
<213> ORGANISM: Artificial sequence
<220> FEATURE:
<223> OTHER INFORMATION: #2 CDR-H1

<400> SEQUENCE: 38

Asp Tyr Trp Met Gln
1               5

<210> SEQ ID NO 39
<211> LENGTH: 16
<212> TYPE: PRT
<213> ORGANISM: Artificial sequence
<220> FEATURE:
<223> OTHER INFORMATION: #56 CDR-H2

<400> SEQUENCE: 39

Met Ile Trp Ala Asp Gly Asp Thr Asp Tyr Asn Ser Ala Leu Lys Ser
1               5                   10                  15

<210> SEQ ID NO 40
<211> LENGTH: 17
<212> TYPE: PRT
<213> ORGANISM: Artificial sequence
<220> FEATURE:
<223> OTHER INFORMATION: #2 CDR-H2

<400> SEQUENCE: 40

Thr Ile Tyr Pro Gly Asp Gly Tyr Thr Arg Tyr Ile Gln Lys Phe Lys
1               5                   10                  15

Gly

<210> SEQ ID NO 41
<211> LENGTH: 12
<212> TYPE: PRT
<213> ORGANISM: Artificial sequence
<220> FEATURE:
<223> OTHER INFORMATION: #56 CDR-H3

<400> SEQUENCE: 41

Asp Ser Tyr Tyr Tyr Gly Tyr Asn Phe Phe Asp Val
1               5                   10

<210> SEQ ID NO 42
<211> LENGTH: 9
<212> TYPE: PRT
<213> ORGANISM: Artificial sequence
<220> FEATURE:
<223> OTHER INFORMATION: #2 CDR-H3
```

```
<400> SEQUENCE: 42

Arg Ala Ala Tyr Tyr Thr Met Asp Tyr
1               5

<210> SEQ ID NO 43
<211> LENGTH: 11
<212> TYPE: PRT
<213> ORGANISM: Artificial sequence
<220> FEATURE:
<223> OTHER INFORMATION: #56 CDR-L1

<400> SEQUENCE: 43

Arg Ala Ser Gln Asp Ile Ser Asn Tyr Leu Asn
1               5                   10

<210> SEQ ID NO 44
<211> LENGTH: 11
<212> TYPE: PRT
<213> ORGANISM: Artificial sequence
<220> FEATURE:
<223> OTHER INFORMATION: #2 CDR-L1

<400> SEQUENCE: 44

Lys Ala Ser Gln Asp Val Asn Thr Ala Val Ala
1               5                   10

<210> SEQ ID NO 45
<211> LENGTH: 7
<212> TYPE: PRT
<213> ORGANISM: Artificial sequence
<220> FEATURE:
<223> OTHER INFORMATION: #56 CDR-L2

<400> SEQUENCE: 45

Tyr Thr Ser Arg Leu His Ser
1               5

<210> SEQ ID NO 46
<211> LENGTH: 7
<212> TYPE: PRT
<213> ORGANISM: Artificial sequence
<220> FEATURE:
<223> OTHER INFORMATION: #2 CDR-L2

<400> SEQUENCE: 46

Trp Ala Ser Thr Arg His Thr
1               5

<210> SEQ ID NO 47
<211> LENGTH: 5
<212> TYPE: PRT
<213> ORGANISM: Artificial sequence
<220> FEATURE:
<223> OTHER INFORMATION: #56 Humanized antibody CDR-H1

<400> SEQUENCE: 47

Gly Tyr Gly Trp Gly
1               5

<210> SEQ ID NO 48
<211> LENGTH: 16
<212> TYPE: PRT
<213> ORGANISM: Artificial sequence
<220> FEATURE:
<223> OTHER INFORMATION: #56 Humanized antibody CDR-H2
```

<400> SEQUENCE: 48

Ser Ile Trp Ala Asp Gly Asp Thr Tyr Tyr Asn Pro Ser Leu Lys Ser
1               5                   10                  15

<210> SEQ ID NO 49
<211> LENGTH: 11
<212> TYPE: PRT
<213> ORGANISM: Artificial sequence
<220> FEATURE:
<223> OTHER INFORMATION: #56 Humanized antibody CDR-L1

<400> SEQUENCE: 49

Gln Ala Ser Gln Asp Ile Ser Asn Tyr Leu Asn
1               5                   10

<210> SEQ ID NO 50
<211> LENGTH: 7
<212> TYPE: PRT
<213> ORGANISM: Artificial sequence
<220> FEATURE:
<223> OTHER INFORMATION: #56 Humanized antibody CDR-L2

<400> SEQUENCE: 50

Tyr Thr Ser Asn Leu Glu Thr
1               5

<210> SEQ ID NO 51
<211> LENGTH: 7
<212> TYPE: PRT
<213> ORGANISM: Artificial sequence
<220> FEATURE:
<223> OTHER INFORMATION: #56 Humanized antibody CDR-L2

<400> SEQUENCE: 51

Tyr Thr Ser Asn Leu Glu Ser
1               5

<210> SEQ ID NO 52
<211> LENGTH: 5
<212> TYPE: PRT
<213> ORGANISM: Artificial sequence
<220> FEATURE:
<223> OTHER INFORMATION: #2 Humanized antibody CDR-H1

<400> SEQUENCE: 52

Asp Tyr Trp Met His
1               5

<210> SEQ ID NO 53
<211> LENGTH: 17
<212> TYPE: PRT
<213> ORGANISM: Artificial sequence
<220> FEATURE:
<223> OTHER INFORMATION: #2 Humanized antibody CDR-H2

<400> SEQUENCE: 53

Ile Ile Tyr Pro Gly Asp Gly Tyr Thr Ser Tyr Ala Gln Lys Phe Gln
1               5                   10                  15

Gly

<210> SEQ ID NO 54
<211> LENGTH: 17
<212> TYPE: PRT
<213> ORGANISM: Artificial sequence
<220> FEATURE:
<223> OTHER INFORMATION: #2 Humanized antibody CDR-H2

-continued

<400> SEQUENCE: 54

Ile Ile Tyr Pro Gly Asp Gly Tyr Thr Ser Tyr Ile Gln Lys Phe Gln
1               5                   10                  15

Gly

<210> SEQ ID NO 55
<211> LENGTH: 11
<212> TYPE: PRT
<213> ORGANISM: Artificial sequence
<220> FEATURE:
<223> OTHER INFORMATION: #2 Humanized antibody CDR-L1

<400> SEQUENCE: 55

Arg Ala Ser Gln Asp Val Asn Thr Ala Leu Ala
1               5                   10

<210> SEQ ID NO 56
<211> LENGTH: 7
<212> TYPE: PRT
<213> ORGANISM: Artificial sequence
<220> FEATURE:
<223> OTHER INFORMATION: #2 Humanized antibody CDR-L2

<400> SEQUENCE: 56

Trp Ala Ser Arg Leu Glu Ser
1               5

<210> SEQ ID NO 57
<211> LENGTH: 7
<212> TYPE: PRT
<213> ORGANISM: Artificial sequence
<220> FEATURE:
<223> OTHER INFORMATION: #2 Humanized antibody CDR-L2

<400> SEQUENCE: 57

Trp Ala Ser Arg Leu Glu Thr
1               5

<210> SEQ ID NO 58
<211> LENGTH: 360
<212> TYPE: DNA
<213> ORGANISM: Artificial sequence
<220> FEATURE:
<223> OTHER INFORMATION: Nucleotide sequence of heavy chain variable
      region of chimeric antibody AB5C1

<400> SEQUENCE: 58
caagtgcagc tgaaggaaag cggccccgga ctggtggccc cttcccagtc cctgagcatc      60
acctgtaccg tgtccggctt ctccctgaca ggctacggag tgaactgggt gaggcagccc     120
cctggaaaag gactggagtg gctcggaatg atttggccg acggcgacac cgattataat      180
tccgccctga gtccaggct gtccatcagc aaggacaaca gcaagtccca agtcttcctc      240
aaggtgaaca acctgcagac cgatgataca gcccggtact actgcgcccg ggactcctac     300
tactacggct acaacttctt cgatgtgtgg ggcgccggaa ccaccgtcac agtgagcagc     360

<210> SEQ ID NO 59
<211> LENGTH: 321
<212> TYPE: DNA
<213> ORGANISM: Artificial sequence
<220> FEATURE:
<223> OTHER INFORMATION: Nucleotide sequence of light chain variable
      region of chimeric antibody AB5C1

<400> SEQUENCE: 59

```
gacatccaga tgacccagac cacatccagc ctcagcgcta gcctgggaga tagggtgaca      60
atctcctgta gggcctccca ggacattagc aactacctga actggtatca gcagaagccc     120
gagggcacac tcaagctgct gatctactac acctcccggc tccatagcgg cgtgccttcc     180
aggtttagcg gctccggctc cggcaccgac tactccctca ccatctcctc cctggaacag     240
gaggacatcg ccacctattt ttgccagcag ggcaacaccc tgcccaggac atttggcggc     300
ggcaccaagc tggagatcaa a                                               321
```

<210> SEQ ID NO 60
<211> LENGTH: 360
<212> TYPE: DNA
<213> ORGANISM: Artificial sequence
<220> FEATURE:
<223> OTHER INFORMATION: Nucleotide sequence of heavy chain variable
      region of humanized antibody AB5C2

<400> SEQUENCE: 60

```
caggtgcagc tgcaggagtc tggaccagga ctggtgaagc cttccgagac cctgagcctg      60
acctgcacag tgtctggctt ctccctgaca ggctacggag tgaactgggt gaggcagcca     120
cctggcaagg gactggagtg gctgggcatg atctgggctg acggcgatac cgactataac     180
tctgccctga gtcccgggt gaccatcagc aaggacacat ctaagaatca gttttccctg     240
aagctgtcca gcgtgaccgc cgctgacaca gctaggtact attgcgcccg ggatagctac     300
tattacggct acaatttctt tgacgtgtgg ggcgctggca ccacagtgac cgtgtcttcc     360
```

<210> SEQ ID NO 61
<211> LENGTH: 321
<212> TYPE: DNA
<213> ORGANISM: Artificial sequence
<220> FEATURE:
<223> OTHER INFORMATION: Nucleotide sequence of light chain variable
      region of humanized antibody AB5C2

<400> SEQUENCE: 61

```
gatatccaga tgacacagtc cccaagctct ctgtctgctt ccgtgggcga cagggtgacc      60
atcacatgtc gggcctccca ggatatcagc aactacctga attggtatca gcagaagcct     120
ggcaaggccc caaagctgct gatctattac acctctaggc tgcactccgg agtgccaagc     180
cggttcagcg gctctggctc cggcaccgac ttcaccttta caatctccag cctgcagcct     240
gaggatatcg ctacatactt ctgccagcag ggcaacaccc tgccaaggac atttggcggc     300
ggcaccaagg tggagatcaa g                                               321
```

<210> SEQ ID NO 62
<211> LENGTH: 360
<212> TYPE: DNA
<213> ORGANISM: Artificial sequence
<220> FEATURE:
<223> OTHER INFORMATION: Nucleotide sequence of heavy chain variable
      region of humanized antibody AB5C6

<400> SEQUENCE: 62

```
caggtgcagc tgaaggagag cggaccagga ctggtggctc atctgagac cctgtccatc      60 acctgtacag tgagcggctt ctctctgaca ggctacggcg tgaattgggt gagacagcca     120
ccaggcaagg gcctggaatg gctgggaatg atctgggctg atggcgacac cgattataac     180
agcgccctga gtctcgcct gacaatctct aaggacaata gcaagtctca ggtgtttctg     240
```

```
aaggtgaaca atctgcagac cgacgataca gctagatatt actgcgcccg cgactcctat      300
tactatggct acaacttctt tgacgtgtgg ggtgccggta ctaccgtcac cgtgtcttct      360

<210> SEQ ID NO 63
<211> LENGTH: 321
<212> TYPE: DNA
<213> ORGANISM: Artificial sequence
<220> FEATURE:
<223> OTHER INFORMATION: Nucleotide sequence of light chain variable
      region of humanized antibody AB5C6

<400> SEQUENCE: 63
gatattcaga tgacccagag ccctagctct ctgtccgcta gcgtgggcga cagagtgacc       60
atctcctgtc gcgccagcca ggatatctct aattacctga actggtatca gcagaagccc      120
gagggcaccc tgaagctgct gatctactat acatccagac tgcatagcgg cgtgccttct      180
cgcttttctg gctccggcag cggcaccgac tactctctga ccatttccag cctgcagcag      240
gaggatatcg ccacctattt ctgtcagcag ggcaataccc tgccaagaac atttggcggc      300
ggcacaaagc tggagatcaa g                                               321
```

ANTI-HUMAN NGF ANTIBODIES AND METHODS USING SAME

FIELD OF THE INVENTION

The invention concerns anti-NGF antibodies (such as anti-NGF antagonist antibodies). The invention further concerns the usage and/or application of the anti-NGF antibody and/or its antigen binding fragments.

BACKGROUND OF THE INVENTION

Nerve growth factor (NGF) is the first discovered neurotrophin, and its role includes both neuron nutrition and neurite growth prompting. NGF plays an important role in regulating the development, differentiation, growth, regeneration and expression of central and peripheral neurons. There are three subunits (α, β and γ) in NGF molecules. β subunits are the active subunits of NGF, and their function are nerve regeneration and repair. By now, there have been two NGF receptors discovered: TrkA tyrosine kinase receptor (high affinity NGF receptor) and p75 common neurotrophin receptor (p75NTR, also called low affinity NGF receptor).

Although the primary function of NGF is to promote the survival and differentiation of neurons, more and more studies have shown that NGF is related to the persistent or chronic pain. In 1993, it was reported that exogenous NGF could induce pain in rats (Lewin G R et al., J Neurosci, 1993, 13:2136-2148). After that, it was found that intravenous NGF in human could induce systemic muscle pain, and local administration also could induce hyperalgesia and abnormal pain at the injection site (petty B G et al., Ann Neurol, 1994, 36:244-246). Other studies have shown that NGF upregulates the expression of neuropeptides in sensory neurons. After binding to TrkA and p75NTR receptors, NGF can increase pain response by up regulating the expression of a sensory neuron—nociceptor, which makes neurons more sensitive to potential pain stimulation (Holmes D, Nat Rev drug discov, 2012, 11:337-338). At present, it has been confirmed the hyper-expression of NGF/TrkA in articular cartilage of degenerative arthritis patients, and the increased expression level of NGF in rheumatic arthritis and interstitial cystitis patients. Thus, development of monoclonal antibodies targeting NGF to inhibit its function is expected to play an active role in the prevention, diagnosis and treatment of various pain related diseases.

There are tens of millions of patients suffering from chronic pain worldwide, and the number is increasing with the population. At present, the drugs of treatment of chronic pain include non-steroidal anti-inflammatory drugs, anticonvulsant drugs, and opioids et al. However, these drugs have been found they have limited efficacy in clinical applications and severe side effects to patients health. For example, besides limited pharmacological efficacy, non-steroidal anti-inflammatory drugs' side effects include gastrointestinal hemorrhage and nephrotoxicity, while the side effect of opioids is addiction. Thus, there is an unmet clinical need for non-opioid, non-toxic and not-easy-abuse new drugs for treatment of acute and chronic pain. Antagonist antibodies targeting NGF has regarded as of great importance for new generation of anti-pain drug development. By now, there have been several anti-human NGF antibodies in different stage of research and development. Tanezumab (from Pfizer/Lilly company) and Fasinumab (from Regeneron/Sanofi company) are the two most advanced antibody candidates. Tanezumab is the first anti-NGF antibody developed for non-opioids based pain treatment. Tanezumab has shown efficacy over a wide range of clinical trials. It has been shown that Tanezumab had highly potent efficacy and analgesic effect on joint pain, chronic low back pain and bladder pain associated with interstitial cystitis (Lane ne et al., n Engl J Med, 2010, 363: 1521-1531). At present, Tanezuma is undergoing phase III clinical trials of indications such as osteoarthritis, back pain, cancer pain, etc. According to the data of phase II/III clinical study on the treatment of osteoarthritis pain with fasinumab, the patients with the four doses of fasinumab treatment group achieved significant improvement in pain relief. Additionally, the clinical trials data of several NGF antibodies also showed that the NGF antibodies may have limited efficacy in severe ill patients, and limited dosage and administration time-period for other patients, which suggests the need of more precise safety exploration of NGF antibodies.

Since NGF is a very important factor in the development of neurons, the amount of NGF in neurons should be taken into careful consideration when developing NGF antibodies. On the one hand, the effective dosage of antibody drugs depends on both the neutralization activity of antigens and the amount of antigens in the body, as the increasement of neutralization activity is related to the decrease of dosage. NGF antibody research needs to discovery novel CDR regions with different affinity for different epitopes or the same epitope. The difference in the immunogenicity of varies CDRs result in different antibody tolerance speed and toxicity, which directly affects the efficacy. On the other hand, the immune response of the subjects to the antibody itself will result in the formation of immune complex, which will change the pharmacokinetics of the antibody, produce unwanted allergic reaction, and finally affect the efficacy of the antibody. Compared with mouse antibody and chimeric antibody, humanized antibody has the lowest immune response to human immune system. The humanized antibody has a similar half-life with natural human antibody, thus ensuring less drug delivery frequency and lower dosage. Therefore, it is of high importance for developing an NGF antibody with good efficacy and safety window to treat or prevent various diseases related to NGF.

BRIEF SUMMARY OF THE INVENTION

The invention disclosed herein concerns a safe and reliable anti-human NGF antibody and/or an antigen-binding fragment targeting human NGF. The antibody and/or its antigen-binding fragment can antagonize the binding of NGF to its receptor (NGF receptor) with high specificity. Therefore, the anti-human NGF antibody and/or its antigen-binding fragment provided by the invention has higher specificity, which is expected to improve the safety profile of the NGF antibody in clinical applications. In addition, the anti-human NGF antibody has higher efficacy, which may reduce the clinical treatment cost.

In another aspect, the invention is a humanized and affinity matured antibody and its antigen binding fragment, which specifically binds to human and rodent nerve growth factor (NGF). The anti-NGF antibody and its antigen binding fragment comprises:

Heavy chain variable region containing CDR-H1, CDR-H2, and CDR-H3 sequences; and Light chain variable region, which includes CDR-L1, CDR-L2 and CDR-L3 sequences, and is selected from the following groups:

(1) The heavy chain variable region includes the CDR-H1 amino acid sequence shown in SEQ ID No. 1, CDR-H2 amino acid sequence shown in SEQ ID No. 3, CDR-H3 amino acid sequence shown in SEQ ID No. 5, CDR-L1 amino acid sequence shown in SEQ ID No. 7, CDR-L2 amino acid sequence having the following 3 amino acids "Tyr Thr Ser", and CDR-L3 amino acid sequence shown in SEQ ID No. 11;

(2) The heavy chain variable region includes the CDR-H1 amino acid sequence shown in SEQ ID No. 2, CDR-H2 amino acid sequence shown in SEQ ID No. 4, CDR-H3 amino acid sequence shown in SEQ ID No. 6, CDR-L1 amino acid sequence shown in SEQ ID No. 8, CDR-L2 amino acid sequence having the following 3 amino acids: Trp Ala Ser and the amino acid sequence of CDR-L3 shown in No. 12;

(3) The heavy chain variable region contains CDR-H1 amino acid sequence shown in SEQ ID No. 37, CDR-H2 amino acid sequence shown in SEQ ID No. 39, CDR-H3 amino acid sequence shown in SEQ ID No. 41, CDR-L1 amino acid sequence shown in SEQ ID No. 43, CDR-L2 amino acid sequence shown in SEQ ID No. 45, and CDR-L3 amino acid sequence shown in SEQ ID No. 11;

(4) The heavy chain variable region contains CDR-H1 amino acid sequence shown in SEQ ID No. 47, CDR-H2 amino acid sequence shown in SEQ ID No. 48, CDR-H3 amino acid sequence shown in SEQ ID No. 41, CDR-L1 amino acid sequence shown in SEQ ID No. 49, CDR-L2 amino acid sequence shown in SEQ ID No. 50, and CDR-L3 amino acid sequence shown in SEQ ID No. 11;

(5) The heavy chain variable region contains CDR-H1 amino acid sequence shown in SEQ ID No. 47, CDR-H2 amino acid sequence shown in SEQ ID No. 48, CDR-H3 amino acid sequence shown in SEQ ID No. 41, CDR-L1 amino acid sequence shown in SEQ ID No. 49, CDR-L2 amino acid sequence shown in SEQ ID No. 51, and CDR-L3 amino acid sequence shown in SEQ ID No. 11;

(6) The heavy chain variable region contains CDR-H1 amino acid sequence shown in SEQ ID No. 38, CDR-H2 amino acid sequence shown in SEQ ID No. 40, CDR-H3 amino acid sequence shown in SEQ ID No. 42, CDR-L1 amino acid sequence shown in SEQ ID No. 44, CDR-L2 amino acid sequence shown in SEQ ID No. 46, and CDR-L3 amino acid sequence shown in SEQ ID No. 12;

(7) The heavy chain variable region contains CDR-H1 amino acid sequence shown in SEQ ID No. 52, CDR-H2 amino acid sequence shown in SEQ ID No. 53, CDR-H3 amino acid sequence shown in SEQ ID No. 42, CDR-L1 amino acid sequence shown in SEQ ID No. 55, CDR-L2 amino acid sequence shown in SEQ ID No. 56, and CDR-L3 amino acid sequence shown in SEQ ID No. 12;

(8) The heavy chain variable region contains CDR-H1 amino acid sequence shown in SEQ ID No. 52, CDR-H2 amino acid sequence shown in SEQ ID No. 53, CDR-H3 amino acid sequence shown in SEQ ID No. 42, CDR-L1 amino acid sequence shown in SEQ ID No. 55, CDR-L2 amino acid sequence shown in SEQ ID No. 57, and CDR-L3 amino acid sequence shown in SEQ ID No. 12;

(9) The heavy chain variable region contains CDR-H1 amino acid sequence shown in SEQ ID No. 52, CDR-H2 amino acid sequence shown in SEQ ID No. 54, CDR-H3 amino acid sequence shown in SEQ ID No. 42, CDR-L1 amino acid sequence shown in SEQ ID No. 55, CDR-L2 amino acid sequence shown in SEQ ID No. 57, and CDR-L3 amino acid sequence shown in SEQ ID No. 12.

Further, the antigen or its antigen binding fragment is mouse derived, chimeric or humanized.

In some embodiments of the invention, the antibody is mouse derived or chimeric, and its heavy chain variable region further comprises the heavy chain fr region of mouse IgG1, IgG2a, IgG2b, IgG3 or variants thereof; and its light chain variable region comprises the light chain fr region of mouse κ, λ chain or variants thereof.

Preferably, the mouse derived or chimeric antibody comprises a heavy chain variable region amino acid sequence as shown in SEQ ID No. 13 or 15 respectively, and a light chain variable region amino acid sequence as shown in SEQ ID No. 14 or 16 respectively.

More preferably, the mouse antibody #56 and the chimeric antibody AB5C1 in the invention comprise a heavy chain variable region amino acid sequence as shown in SEQ ID No. 13 and a light chain variable region amino acid sequence as shown in SEQ ID No. 14.

More preferably, the mouse antibody #2 and the chimeric antibody ab5d1 in the invention comprise a heavy chain variable region amino acid sequence as shown in SEQ ID No. 15 and a light chain variable region amino acid sequence as shown in SEQ ID No. 16.

In some embodiments of the invention, the antibody is humanized. The preparation of humanized antibody can be completed by CDR transplantation technology, surface remodeling technology, computer simulation technology or other existing technologies.

In some embodiments of the invention, the mouse antibody Chen 56 is humanized by CDR transplantation. The resulting humanized antibody, preferably, has a heavy chain variable region containing an amino acid sequence selected from SEQ ID NOS: 17, 19, 21 or 23, and a light chain variable region containing an amino acid sequence selected from SEQ ID NOS: 18, 20, 22 or 24. More preferably, the resulting humanized antibodies AB5C2, ab5c3, ab5c4 and ab5c5, wherein the heavy chain variable region respectively comprises an amino acid sequence as shown in SEQ ID No. 17, 19, 21 or 23, and the light chain variable region respectively comprises an amino acid sequence as shown in SEQ ID No. 18, 20, 22 or 24.

In some embodiments of the invention, the mouse antibody Chen 56 is humanized by surface remodeling technology. Preferably, the resulting humanized antibody AB5C6 has a heavy chain variable region containing an amino acid sequence as shown in SEQ ID No. 25, and a light chain variable region containing an amino acid sequence as shown in SEQ ID No. 26.

In some embodiments of the invention, the mouse antibody Chen 2 is humanized by CDR transplantation. The resulting humanized antibody preferably has a heavy chain variable region containing an amino acid sequence selected from SEQ ID NOS: 27, 29, 31 or 33, and a light chain variable region containing an amino acid sequence selected from SEQ ID NOS: 28, 30, 32 or 34. More preferably, the resulting humanized antibodies ab5d2, ab5d3, ab5d4 and ab5d5, wherein the heavy chain variable region respectively comprises an amino acid sequence as shown in SEQ ID No. 27, 29, 31 or 33, and the light chain variable region respectively comprises an amino acid sequence as shown in SEQ ID No. 28, 30, 32 or 34.

In some embodiments of the invention, the mouse antibody #2 is humanized by surface remodeling technology. Preferably, the resulting humanized antibody ab5d6 has a heavy chain variable region containing an amino acid sequence as shown in SEQ ID No. 35, and a light chain variable region containing an amino acid sequence as shown in SEQ ID No. 36.

Without substantially affecting the antibody activity, those skilled in the art may replace, add or reduce one or more (e.g., 1, 2, 3, 4, 5, 6, 7, 8, 9 or 10 or more) amino acids of the sequence of the antibody of the invention to obtain a variant of the antibody sequence. They are all considered to be included in the scope of protection of the invention. For example, amino acids with similar properties will be substituted in the variable region. The sequence of the variant of the invention can be at least 80% homologous with its source sequence; more preferably, the sequence of the variant of the invention can be at least 85%, 90%, 95%, 96%, 97%, 98% or 99% homologous with its source sequence.

In some embodiments of the invention, the antibody and/or its antigen binding fragment provided by the present invention is a full-length antibody that further comprises an antibody constant region of a human or mouse; or an antigen binding fragment that only contains fab, Fab', f (ab') 2 or scFv.

In a preferred example of this aspect, the heavy chain constant region sequence is selected from human IgG1, IgG2, IgG3 or IgG4.

In a preferred example in this respect, the light chain constant region sequence of the antibody or its antigen binding fragment is a human κ antibody light chain constant sequence.

In one embodiment of the invention, the antibody binds to a human NGF. Specifically, the antibody can block the interaction between human NGF and corresponding human NGF receptor. Kd value of the antibody or its antigen binding fragment binding to NGF is $\leqslant 5\times10^{-11}$ m, preferably $1\times10^{-11}$ m or smaller KD.

In a second aspect of the invention, a polynucleotide sequence encoding the antibody or the antigen binding fragment thereof is provided. Preferably, the polynucleotide sequence encoding the heavy chain variable region of the antibody or its antigen binding fragment is as shown in SEQ ID No. 58, 60 and 62 respectively, and the polynucleotide sequence encoding the light chain variable region of the antibody or its antigen binding fragment is as shown in SEQ ID No. 59, 61 and 63 respectively.

For example, the polynucleotide sequence encoding the heavy chain variable region of the chimeric antibody AB5C1 preferred by the present invention is shown in SEQ ID No. 58, and the DNA molecule encoding the light chain variable region is shown in SEQ ID No. 59.

For example, the polynucleotide sequence encoding the heavy chain variable region of the humanized antibody AB5C2 preferred by the invention is shown in SEQ ID No. 60, and the DNA molecule encoding the light chain variable region is shown in SEQ ID No. 61.

As another example, the polynucleotide sequence encoding the heavy chain variable region of the humanized antibody AB5C6 is shown in SEQ ID No. 62, and the DNA molecule encoding the light chain variable region is shown in SEQ ID No. 63.

In a third aspect of the present invention, there is provided an expression vector comprising the polynucleotide sequence.

In a fourth aspect of the invention, a host cell transfected with the expression vector is provided. Preferably, the host cell is CHO cell.

In a fifth aspect of the invention, a pharmaceutical composition is provided. The pharmaceutical composition comprises at least one pharmaceutically acceptable carrier, excipient or diluent, and an effective amount of the antibody or its antigen binding fragment.

The sixth aspect of the invention provides the use of the antibody or its antigen binding fragment or pharmaceutical composition, preferably for the treatment of any disease related to NGF, in particular pain disease related to NGF.

These diseases are usually related to the overexpression and elevation of NGF. The diseases include but are not limited to degenerative arthritis, rheumatic arthritis, interstitial cystitis, osteonecrosis, low back pain or diabetic peripheral neuropathy, etc.

Preferably, a chimeric, humanized anti NGF antibody and its antigen binding fragment can be used in the preparation of a drug for treating the disease; more preferably, a humanized anti NGF antibody and its antigen binding fragment can be used.

The invention discloses that the antibody provided by the invention or the antigen binding fragment thereof has the following advantages:

1. The antibody provided by the invention has high affinity, and the affinity constant Kd value is $\leqslant 5\times10^{-11}$M, which can effectively block the binding between NGF and its receptor, and block the response of pain;

2. The antibody provided by the invention has strong specificity of binding with antigen, and it can be expected that the clinical dosage will also be reduced;

3. The antibody provided by the invention is expressed by CHO cells and has the advantages of high yield, high activity, simple purification process and low production cost.

DESCRIPTION OF THE INVENTION

Abbreviation and Definition hNGF human neuron growth factor
CDR complementary determination region in immunoglobin proteins variable region which is defined by IMGT system
ELISA enzyme linked immunosorbent assay
FR framework region
HRP Horseradish peroxidase
IgG Immunoglobulin G
Kabat Immunoglobulin protein comparison and coding system advocated by Elvin a Kabat
IMGT International immunogenetic information system proposed by LaFranc et al
mAb monoclonal antibody
PCR polymerase chain reaction
V region IgG chain fragment with variable sequence between different antibodies. It extends to 109 residues of light chain and 113 residues of heavy chain.
VH Immunoglobulin heavy chain variable region
VK Immunoglobulin kappa light chain variable region
$K_D$ equilibration constant
kd dissociation rate constant
kon association rate constant Definitions The term "antibody" as used in the present invention refers to the immunoglobulin molecule and the immunoactive part of the immunoglobulin molecule, that is, the molecule containing the antigen binding site of the specific binding antigen, covering the full-length antibody (e.g., IgG1 or IgG4 antibody), various functional segments (e.g., may only contain the antigen binding part, such as Fab, f (ab') 2 or scFv segments), and modified Antibodies (e.g. humanization, glycosylation, etc.). Examples of antibodies include, but are not limited to, polyclonal antibodies, monoclonal antibodies, chimeric antibodies, humanized antibodies, domain antibodies, single chain antibodies, Fab, Fab', f (ab') 2 fragments, etc. The invention also includes an anti NGF antibody with glycosylation modification. In some applications, modification can be carried out to remove undesirable glycosylation sites, such as fucose modification on oligosaccharide chain to enhance the function of antibody dependent cytotoxicity (ADCC); in other applications, galactosylation can be carried out to change complement dependent cytotoxicity (CDC)

The term "monoclonal antibody or mAb" refers to an antibody obtained from a single clone cell line, which is not limited to a eukaryotic, prokaryotic or phage clone cell line. Monoclonal antibodies or antigen binding fragments can be reconstructed by hybridoma technology, recombinant technology, phage display technology, synthetic technology (such as CDR grafting), or other existing technologies.

"Antibody fragment" and "antigen binding fragment" mean the antigen binding fragment and antibody analogue of an antibody, which generally includes the antigen binding region or variable region (e.g. one or more CDRs) of at least part of the parent antibody. Antibody fragments retain at least some binding specificity of the parent antibody. In general, when the activity is expressed on a molar basis, the antibody fragment retains at least 10% of the maternal binding activity. Preferably, the antibody fragment retains at least 20%, 50%, 70%, 80%, 85%, 90%, 95% or 100% or more of the binding affinity of the parent antibody to the target. Examples of antibody fragments include, but are not limited to: fab, Fab', f (ab') 2 and Fv fragments; double antibodies; linear antibodies; single chain antibody molecules, such as scFv, single antibody (technology from genmab); nano antibody (technology from domanti s); domain antibody (technology from Ablynx); and multi-specific antibody formed by antibody fragments. Antibody variants of engineering modification are summarized in Holliger et al., NAT biotechnology, 2005, 23:1126-1136.

"Fab fragment" consists of CH1 and variable region of a light chain and a heavy chain. The heavy chain of Fab molecule cannot form disulfide bond with another heavy chain molecule.

"The Fab' fragment" contains VH domain and CH1 domain of one light chain and one heavy chain, and the constant region between CH1 and CH2 domain. Thus, the intermolecular disulfide bond can be formed between the two heavy chains of two Fab' fragments to form f (ab') 2 molecule.

The "F (ab') 2 fragment" contains VH domain and ch1 domain of two light chains and two heavy chains, as well as the constant region between ch1 and CH2 domains, thus forming an inter chain disulfide bond between the two heavy chains. Therefore, the f (AB') 2 fragment consists of two Fab fragments which are held together by the disulfide bond between two heavy chains.

"FV region" contains variable region from heavy chain and light chain, but it lacks constant region.

"ScFv antibody" or "scFv antibody" refers to the antibody fragments containing VH and VL domains of the antibody, where these domains exist in a single polypeptide chain. For a review of scFv, see pluckthun, 1994, the pharmacology of monoclonal antibodies, Vol. 113, edited by Rosenburg and Moore, Springer Verlag, Berlin, Heidelberg, pp. 269-315. See also international patent application Publication No. wo88/01649 and U.S. Pat. No. 4,946,778 and No. 5260203.

The "FC" region contains two heavy chain fragments of ch1 and CH2 domains containing antibodies. The two heavy chain segments are held together by two or more disulfide bonds and through the hydrophobic action of the CH3 domain.

"Antigen binding fragment" is an immunoglobulin fragment with immunological function, which only contains heavy chain variable region or light chain variable region chain.

The term "hypervariable region" or "CDR region" or "complementary determining region" as used herein refers to the amino acid residues of antibodies responsible for antigen binding. The CDR region sequence can be defined by IMgt, Kabat, chothia and ABM methods or identified by any CDR region sequence determination method well known in the art. Antibody CDR can be identified as hypervariable regions initially defined by Kabat et al., for example, 24-34 (L1), 50-56 (L2) and 89-97 (L3) residues in light chain variable domains and 31-35 (H1), 50-65 (H2) and 95-102 (H3) residues in heavy chain variable domains. See Kabat E A et al., 1991, sequences of proteins of immune interest, public health service, National Institutes of health, Bethesda, Md.; the location of CDR can also be identified as originally defined by the "hypervariable ring" (HVL) structure described by chothia et al. IMgt (immunogenetics) also provides a numbering system for immunoglobulin variable region including CDR. CDR region is defined according to IMgt number, for example, 27-32 (L1), 50-52 (L2) and 89-97 (L3) residues of light chain variable domain and 26-35 (H1), 51-57 (H2) and 93-102 (H3) residues of heavy chain variable domain. See e.g. Lefranc M P, etc., dev comp Immunol, 2003, 27:55-77, incorporated herein by reference. Other methods for CDR identification include "ABM definition", which is a compromise between Kabat and chothia and is obtained by Oxford molecular's ABM antibody model software; or "contact definition" of CDR, which is based on the observed antigen contact and described in MacCallum R M et al., J. Mol Biol, 1996, 262:732-745. In the "configuration definition" method of CDR, the position of CDR can be identified as the residue contributing to the cooperative enthalpy of the original junction. For example, makabe K et al., J Biol Chem, 2008, 283:1156-1166. The methods used in the present invention may be defined by or according to CDR defined by any of these methods, including but not limited to any of Kabat definition, IMgt definition, chothia definition, ABM definition, contact definition and/or configuration definition.

The term "chimeric antibody" refers to an antibody fused with the variable region of mouse antibody and the constant region of human antibody, which can reduce the immune response induced by mouse antibody. To establish chimeric antibody, we need to select hybridoma secreting mouse specific monoclonal antibody, clone variable region gene from mouse hybridoma cell, clone constant region gene of human antibody as required, connect variable region gene of mouse and constant region gene of human into chimeric gene, insert it into vector, and express chimeric antibody molecule in eukaryotic expression system or prokaryotic expression system In a preferred embodiment of the present invention, the antibody light chain variable region of the NGF chimeric antibody further comprises the light chain fr region of mouse source κ, λ chain or variants thereof. The antibody heavy chain variable region of the NGF chimeric antibody further comprises the heavy chain fr region of mouse derived IgG1, IgG2a, IgG2b or IgG3 or variants thereof. The constant region of human antibody can be selected from the constant region of heavy chain of human IgG1, IgG2, IgG3 or IgG4 or their variants, preferably including the constant region of heavy chain of human IgG1.

"Humanized" non-human (such as mouse) antibodies are chimeric antibodies that contain the minimum sequence of non-human immunoglobulins. For the most part, humanized antibodies are human immunoglobulins (recipient antibodies) in which the recipient hypervariable region residue is replaced by the hypervariable region residue of non-human sources (donor antibodies) (such as mice, rats, rabbits or non-human primates antibodies that require specificity, affinity and activity). In some cases, the fr residues of human immunoglobulin can be replaced by the corresponding non-human residues. In addition, humanized antibodies may include residues that neither exist in the recipient antibody nor in the donor antibody. These modifications can further improve the performance of the antibody. Generally, humanized antibody contains all (at least one, usually two) variable regions, in which all or basically all high variable regions correspond to the high variable regions of non-human immunoglobulin, and all or basically all fr regions are fr regions of human immunoglobulin sequence. Humanized antibodies preferably also include at least a portion of the constant region (FC) of the immunoglobulin (usually human immunoglobulin). For more details, please refer to references Jones Pt et al., nature, 1986, 321: 522-525.

The terms "immunobinding" and "immunobinding properties" used in this paper refer to a non covalent interaction between immunoglobulin molecules and antigens for which immunoglobulins are specific. The intensity or affinity of immune binding interaction can be expressed by the equilibrium dissociation constant (KD). The smaller the Kd value is, the higher the affinity is. The immunobinding properties of the selected polypeptide can be quantified by a method known in the art. One method involves measuring the rate of formation and dissociation of antigen binding sites/antigen complexes. Both "binding rate constant" (KA or Kon) and "dissociation rate constant" (KD or koff) can be calculated by the concentration and the actual rate of association and dissociation (Malmqvist m, nature, 1993, 361: 186-187). The ratio of KD/Kon is equal to the dissociation constant KD (usually see Davies et al., annual Rev Biochem, 1990, 59:439-473). KD, Kon and KD can be measured by any effective method. In a preferred embodiment, the dissociation constant is measured by a bioluminescent interferometry, such as the fortebio octet method described in example 3. In other preferred embodiments, the dissociation constant may be measured using a surface plasmon resonance technique such as Biacore or kinexa. When the equilibrium binding constant (KD) is $\leq 5\times10^{-11}$ m, preferably $\leq 1\times10^{-11}$ m, the antibody of the invention is considered to specifically bind to the NGF epitope.

The term "labeled" or "labeled" as used herein refers to the incorporation of a detectable marker, such as an amino acid by incorporation of a radioactive marker or the attachment of a biotin module to a polypeptide that can be detected by a labeled affinity, such as a streptomycin containing a fluorescent marker or an enzymatic activity that can be detected by optical or calorimetric methods. In some cases, markers or markers can also be therapeutic. Various methods for labeling polypeptides and glycoproteins are known and can be used in the art. Examples of markers for polypeptides include, but are not limited to, radioisotopes or radionuclides (such as 3 h, 14C, 15N, 35S, 90Y, 99Tc, 111In, 125I, 131I), fluorescent markers (such as FITC, rhodamine, lanthanide phosphors), enzyme markers (such as horseradish peroxidase, p-galactosidase, fluorescent enzyme, alkaline phosphatase), chemiluminescence, biotin group, predetermined peptide epitope recognized by secondary reporter (such as leucine zipper pair sequence, binding site of secondary antibody, metal binding domain, epitope label).

Homologous Antibody

In another aspect, the amino acid sequence contained in the heavy chain and light chain variable region of the antibody of the invention is homologous with the amino acid sequence of the preferred antibody described herein, and the antibody retains the desired functional characteristics of the anti NGF antibody of the invention.

For example, the invention provides humanized antibody or antigen binding fragment of NGF, which includes heavy chain variable region and light chain variable region, wherein: (a) the heavy chain variable region includes amino acid sequence at least 80% homologous with amino acid sequence selected from SEQ ID NOS: 17, 19, 21, 23, 25, 27, 29, 31, 33 or 35; more preferably, the heavy chain variable region includes amino acid sequence selected from SEQ ID NOS: amino acid sequence of 17, 19, 21, 23, 25, 27, 29, 31, 33 or 35 is at least 85%, 90%, 95%, 96%, 97%, 98% or 99% homologous; (b) the light chain variable region contains and is selected from seq ID NOS: amino acid sequences of 18, 20, 22, 24, 26, 28, 30, 32, 34 or 36 are at least 80% homologous; more preferably, the light chain variable region comprises amino acid sequences of at least 85%, 90%, 95%, 96%, 97%, 98% or 99% homologous with amino acid sequences selected from SEQ ID NOS: 18, 20, 22, 24, 26, 28, 30, 32, 34 or 36.

Antibody with Conservative Modification

The term "conservative modification" is intended to mean that amino acid modification does not significantly affect or alter the binding characteristics of antibodies containing the amino acid sequence. These conserved modifications include substitution, addition and deletion of amino acids. The modification can be introduced into the antibody of the invention through the advantages of standard techniques known in the art, such as site directed mutagenesis and PCR mediated. Conservative amino acid substitution refers to the substitution of amino acid residues with amino acid residues with similar side chains. A family of amino acid residues having similar side chains has been described in detail in the art. These families include those with basic side chains (e.g. lysine, arginine, histidine), acid side chains (e.g. aspartic acid, glutamic acid), polar side chains without charge (e.g. glycine, asparagine, glutamine, serine, threonine, tyrosine, cysteine, tryptophan), nonpolar side chains (e.g. alanine, valine, leucine, isoleucine Amino acids of, proline, phenylalanine, methionine, β-branched side chains (such as threonine, valine, isoleucine) and aromatic side chains (such as tyrosine, phenylalanine, tryptophan, histidine). Therefore, one or more amino acid residues in the CDR region of the antibody of the invention can be replaced with other amino acid residues from the same chain family.

In some embodiments of the invention, the antibodies of the present invention include heavy chain variable regions containing CDR-H1, CDR-H2 and CDR-H3 sequences and light chain variable regions containing CDR-L1, CDR-L2 and CDR-L3 sequences, wherein one or more of these CDR sequences contain specific amino acid sequences or conservative modifications based on the preferred antibodies herein, and the antibodies retain the period of the anti NGF antibodies of the present invention Functional characteristics of hope. Therefore, the invention provides a separated binding NGF antibody or an antigen binding part thereof, which comprises a heavy chain variable region containing CDR-H1, CDR-H2 and CDR-H3 sequences and a light chain variable region containing CDR-L1, CDR-L2 and CDR-L3 sequences, wherein: (a) the heavy chain variable region CDR-H1 sequence comprises a light chain variable region selected from SEQ ID The amino acid sequence shown in No. 1 and 2 and its conservatively modified amino acid sequence; and/or the heavy chain variable region CDR-H2 sequence includes the amino acid sequence selected from the amino acid sequence shown in SEQ ID No. 3 and 4 and its conservatively modified amino acid sequence; and/or the heavy chain variable region CDR-H3 sequence includes the amino acid sequence selected from the SEQ ID Amino acid sequences shown in No. 5 and 6 and their conservatively modified amino acid sequences; and/or (b) the light chain variable region CDR-L1 sequence comprises amino acid sequences selected from the amino acid sequences shown in SEQ ID No. 7 and 8 and their conservatively modified amino acid sequences; and/or the light chain variable region CDR-L2 sequence comprises amino acid sequences selected from the SEQ ID The amino acid sequences shown in No. 9 and 10 and their conservatively modified amino acid sequences; and/or the light chain variable region CDR-L3 sequences comprise amino acid sequences selected from those shown in SEQ ID NOS: 11 and 12 and their conservatively modified amino acid sequences.

McAb Production

The monoclonal antibody of the invention can be prepared by a variety of technologies, including conventional monoclonal antibody methodology, such as standard somatic hybridization technology described in Kohler g and Milstein C, nature, 1975:256:495. Although somatic hybridization procedures are preferred, other methods for the preparation of monoclonal antibodies, such as virus or carcinogenic transformation of B lymphocytes, may also be used in principle.

The preferred animal system for hybridoma preparation is mouse family. It is a perfect procedure to prepare hybridoma in mice. It is known in the art that the immune scheme and technology for separating the immune spleen cells for fusion. Fusion mates (such as mouse myeloma cells) and fusion procedures are also known.

In order to express antibodies and their antibody fragments, the polynucleotide sequence encoding partial or full-length light and heavy chains can be obtained by standard molecular biological techniques (such as PCR amplification or cDNA cloning of hybridoma expressing the target antibody), and the polynucleotide sequence can be inserted into the expression vector, so that the target gene can be operatively linked with transcription and translation regulatory sequence, and then transferred to the host cell for expression The expression host preferred eukaryotic expression vector, more preferred mammalian cells, such as CHO and its derived cell lines.

Antibodies can be purified by well-known techniques, such as affinity chromatography using protein A or protein G. Subsequently or alternatively, the specific antigen or its epitope may be immobilized on a column to purify the immune specific antibody by immunoaffinity chromatography. Purification of immunoglobulins was discussed by Wilkinson D, for example (the scientist, 2000, 8:25-28, the scientist, Inc., Philadelphia Pa.).

The chimeric or humanized antibody of the invention can be prepared according to the sequence of the prepared mouse monoclonal antibody. Polynucleotide sequence encoding heavy and light chain immunoglobulins can be obtained from target mouse hybridomas and engineered to contain non mouse (e.g., human) immunoglobulin sequences using standard molecular biology techniques. For example, in order to create chimeric antibodies, a method known in the art can be used to connect a mouse variable region to a human constant region (see U.S. Pat. No. 4,816,567, for example, cabilly et al.). The separated DNA encoding VH region can be transformed into full-length heavy chain gene by another polynucleotide sequence operatively connecting VH coding DNA to coding heavy chain constant region (ch1, CH2 and CH3). The sequence of human heavy chain constant region gene is known in the field (see, for example, Kabat E A et al., 1991, sequences of proteins of immune interest, public health service, National Institutes of health, Bethesda, Md.). DNA fragments containing these regions can be amplified by standard PCR. The heavy chain constant region can be IgG1, IgG2, IgG3, IgG4, IgA, IgE, IgM or IgD constant region, but the most preferred region is IgG1 or IgG4 constant region.

In order to create humanized antibodies, the method known in the art can be used to insert the mouse CDR region into the human frame sequence (see U.S. Pat. No. 5,225,539 of winter and U.S. Pat. Nos. 5,530,101; 5,585,089; 5,693,762 and 6,180,370 of queen, etc.). It is also possible to utilize transgenic animals, such as humAb mice (medarex, Inc.) that contain human immunoglobulin gene microloci (miniloci) encoding non rearranged human heavy chain (μ and γ) and κ light chain immunoglobulin sequences, in addition to targeted mutations that inactivate endogenous μ and κ chain loci (see, for example, lonberg et al., nature, 1994, 368: 856-859); or "KM mouse TM" (see patent wo02/43,478) carrying human heavy chain transgene and human light chain chromosomal transformation for antibody humanization. Other methods of humanization include surface remodeling and phage display.

The invention is further described by the following embodiments, which shall not be construed as further limiting. All drawings and all references, patents and published patent applications quoted in the whole application are hereby expressly included as references.

FIGURE LEGENDS

FIG. 1. Indirect ELISA was used to determine the binding titer of different monoclonal antibodies against human NGF mice.

Figure 2:
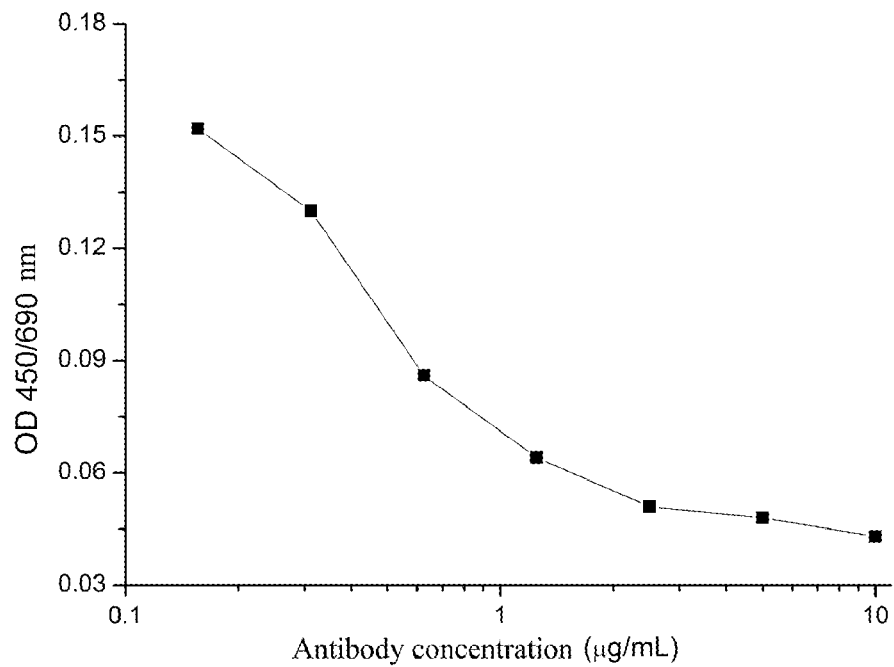

FIG. 2. Competitive ELISA was used to determine the ability of anti human NGF mouse monoclonal antibody Chen 56 to block the binding of hNGF and its receptor TrkA.

FIG. 3-1. The parallel comparison of amino acid sequences of AB5C2, ab5c3, ab5c4, ab5c5 and AB5C6 with the heavy chain variable region of mouse antibody #56. Where the underline is the CDR area sequence (as defined by the IMgt system).

FIG. 3-2. Parallel comparison of amino acid sequences of AB5C2, ab5c3, ab5c4, ab5c5 and AB5C6, which are humanized antibodies against hNGF, with those of mouse antibody #56 light chain variable region. Where the underline is the CDR area sequence (as defined by the IMgt system).

4-1. Parallel comparison of amino acid sequences of ab5d2, ab5d3, ab5d4, ab5d5 and ab5d6 humanized antibodies against hNGF with that of #2 heavy chain variable region of mouse antibody. Where the underline is the CDR area sequence (as defined by the IMgt system).

FIG. 4-2. The parallel comparison of the amino acid sequences of ab5d2, ab5d3, ab5d4, ab5d5 and ab5d6, which are humanized antibodies against hNGF, with that of the light chain variable region of mouse antibody #2. Where the underline is the CDR area sequence (as defined by the IMgt system).

Figure 5:
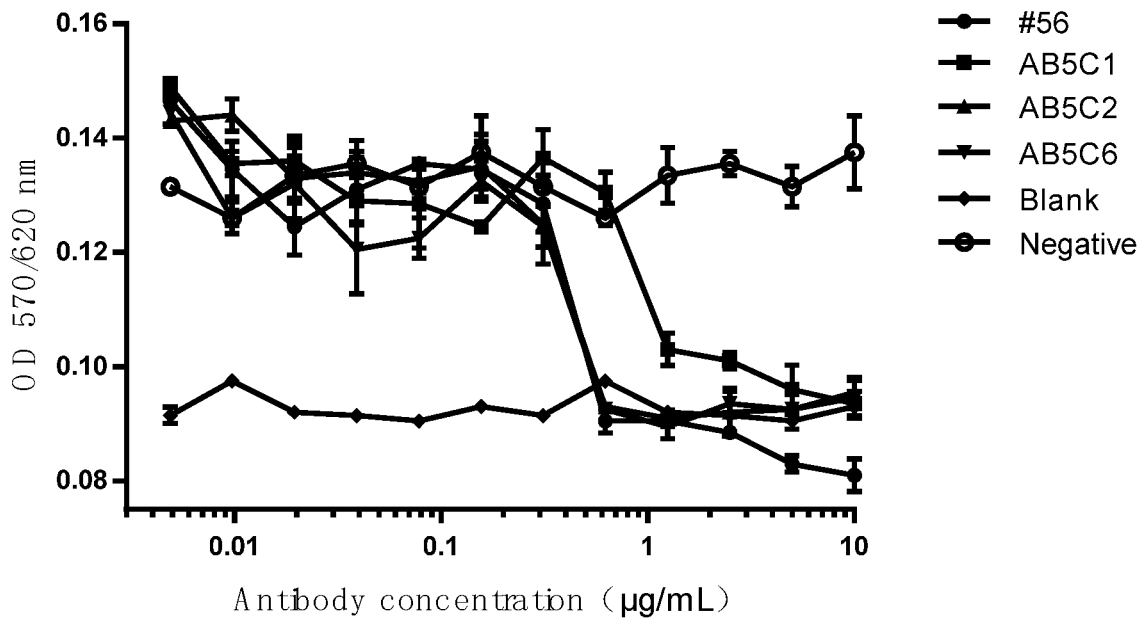

FIG. 5. Detection of anti-hngf antibody inhibiting NGF dependent cell survival signal.

6. Effect of AB5C1 on wound model after operation. Note: compared with the model group, * * P<0.01, * * * P<0.001.

Figure 7:
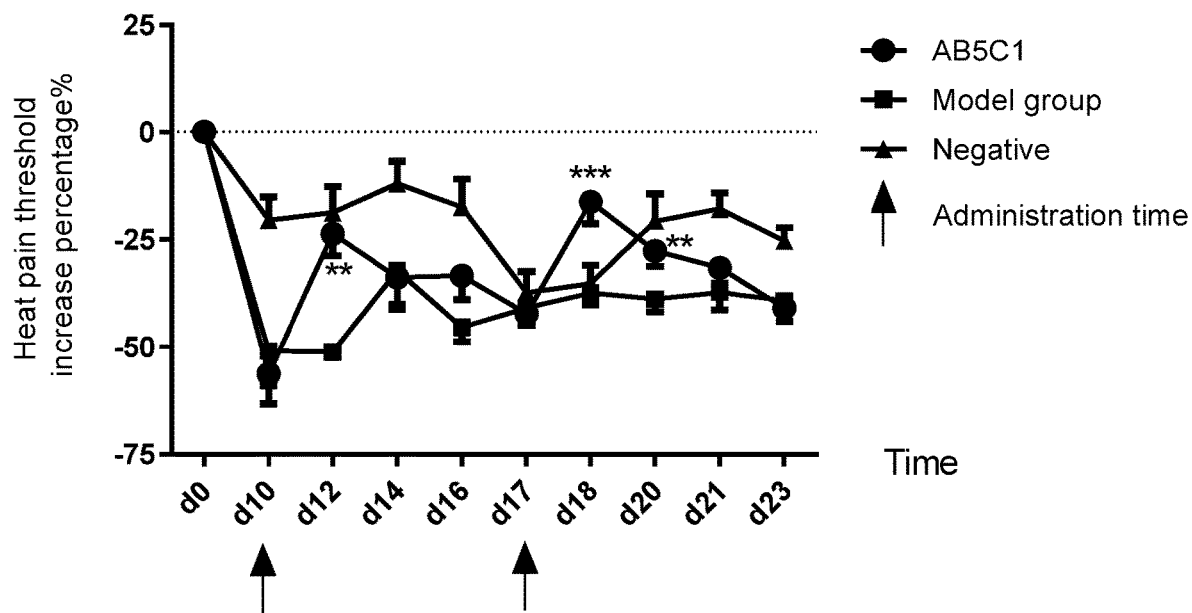

FIG. 7. The effect of AB5C1 on the sciatic nerve ligation model in some mice. Note: compared with the model group, * * P<0.01, * * * P<0.001.

Figure 8:
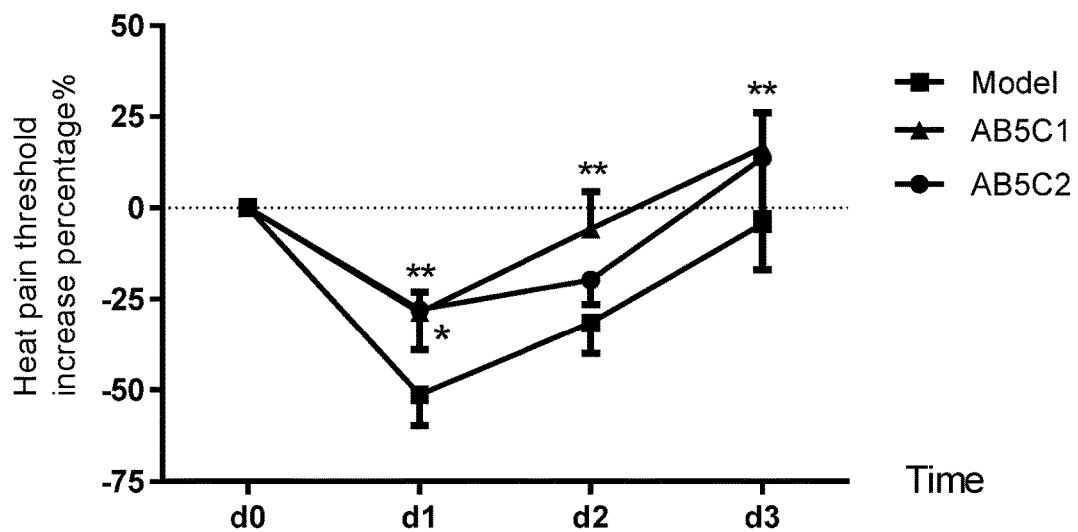

FIG. 8. Effect of AB5C1 and AB5C2 on acute gouty arthritis model induced by sodium urate. Note: compared with the model group, * P<0.01, * P<0.05.

Figure 9:
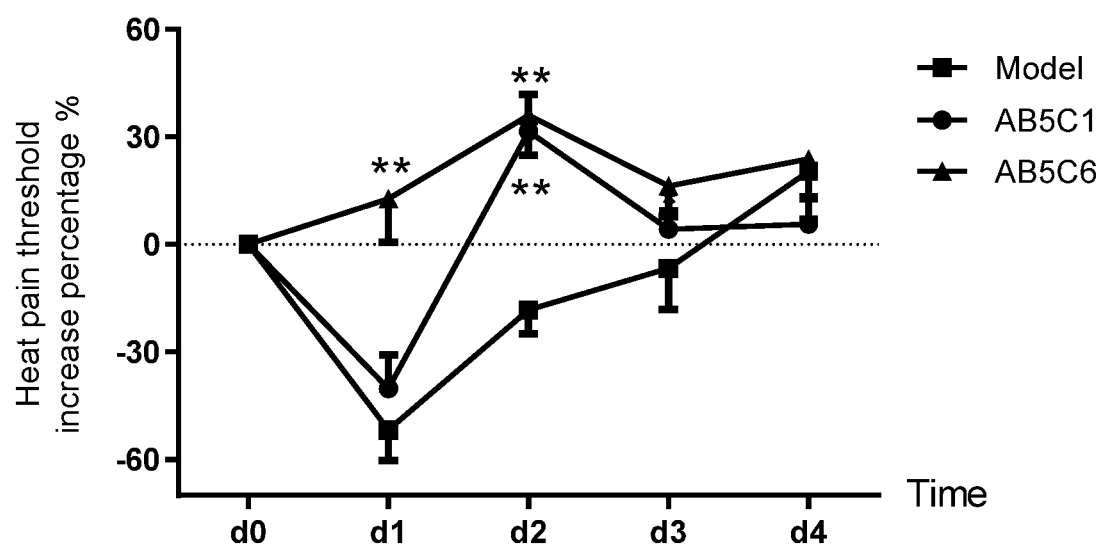

FIG. 9. Effects of AB5C1 and AB5C6 on complete Freund's adjuvant induced inflammatory pain model. Note: compared with the model group, * P<0.01, * P<0.05.

EXAMPLES

Example 1. Preparation of Monoclonal Antibody Against hNGF

Four week old BALB/c mice were immunized subcutaneously with recombinant human NGF (peprotech company) and 20 μg/mouse fully emulsified with Freund's adjuvant. The immune cycle was three weeks. On the 10th day after the third immunization, blood was collected from the eye socket, and the titer of anti human NGF antibody was tested by ELISA to monitor the immune response of mice. The mice with the highest titer of anti human NGF antibody were immunized once three days before fusion. After 3 days, the spleen of the mouse was taken out and fused with the myeloma SP2/0 cell line. Mixed $5 \times 10^8$ SP2/0 cells and $5 \times 10^8$ mouse spleen cells were fused in 50% PEG (molecular weight 1450) and 5% DMSO solution. The number of spleen cells was adjusted to $7.5 \times 10^5$/ml with Iscove medium (containing 10% fetal bovine serum, 100 U/ml penicillin, 100 μg/ml streptomycin, 0.1 mm hypoxanthine, 0.4 μm aminopterin and 16 μm thymidine), and 0.2 ml was added into 96 well plate. Placed in an incubator at 37° C. with 5% CO2. After 10 days, the high-throughput ELISA method was used to detect the ability of the antibody in the supernatant to compete with the FC labeled human TrkA receptor to bind to hNGF, so as to screen out the positive clones competing with the human TrkA receptor (see example 3 for the method). After subcloning the hybridoma cells, three positive hybridoma cell lines A2, A56 and A98 were screened out by competitive ELISA.

Clones of specific antibodies were cultured in RPMI 1640 supplemented with 10% FCS. When the cell density reached about $5 \times 10^5$ cells/ml, the medium was replaced by serum-free medium. After 2 to 4 days, the culture medium was centrifuged to collect the supernatant. Protein G column was used to purify the antibody. The monoclonal antibody eluate was dialyzed with 150 mM NaCl. The dialyzed solution was filtered through a 0.2 μm filter to get the purified mouse monoclonal antibodies #2, #56 and #98.

Example 2. Titer Determination of Anti hNGF Mouse Antibody

Indirect ELISA was used to determine the binding titers of purified mouse antibody #2, #56 and #98 to hNGF. Among them, each pore was coated with 100 μl 0.2 μg/ml hNGF (Corning company) and placed at 4° C. for 16-20 h. The PBS buffer in 96 well plate was sucked off, washed with PBST (pH 7.4, PBS containing 0.05% Tween 20) buffer once, then 200 μL/well PBST/1% skimmed milk powder was added, incubated at room temperature for 1 h and sealed. Remove the blocking solution, wash the plate with PBST buffer for 3 times, add PBST/1% skimmed milk powder to dilute to the appropriate concentration of anti-hngf mouse antibody to be tested, 100 μL/well, incubate at room temperature for 1.5 h. Remove the reaction system, wash the plate with PBST three times, and then use the HRP labeled Sheep anti mouse IgG polyclonal antibody (Jackson Laboratory) diluted with PBST/1% skimmed milk powder (dilution ratio 1:5000) at 50 μL/well as the detection antibody, and incubate at room temperature for 1 h. After 3 times of PBST washing, add 100 μL/well TMB and incubate at room temperature for 10-30 min. Add 50 μL/pore 0.2 M sulfuric acid to stop the reaction. The absorbance value was detected at OD450 nm by enzyme labeling instrument, and the result is shown in FIG. 1.

It can be seen from FIG. 1 that mouse antibody #2, #56 and #98 can all bind to hNGF, and the binding potency of #56 is the best.

Example 3. Binding Inhibition Assay of Anti-hNGF Mouse Antibody and NGF Receptor TrkA The enzyme plate was coated with 100 μl 2.5 μg/ml hNGF at room temperature overnight. Discard the coated solution, seal the holes with skimmed milk dissolved in PBS for 0.5 h, and wash the holes with PBST. Then add 50 μL 2 μg/ml of TrkA (Beijing Yiqiao Shenzhou Biology) labeled with human Fc and 50 μl of mixed solution with different concentrations of #56 antibody (10-0.15 μg/ml). The human IgG Fc polyclonal antibody (Jackson Laboratory) labeled with HRP was used as the detection antibody, and the OD450/690 nm absorbance was recorded by TMB. It can be seen from FIG. 2 that #56 antibody can specifically block the binding of NGF to trkA.

Example 4. Affinity Analysis Assay of Anti-hNGF Mouse Antibody

The binding affinity constants of purified mouse monoclonal antibody #56 and #2 with antigens were determined by the bio film interference technique (fortebio octet Red & QK system, Pall company). The concentration gradient of multichannel parallel quantitative analysis was set as 3.125, 6.25, 12.5, 25, 50 and 100 nm, and human NGF (his tag) was affinity coupled to Ni NTA sensor. After the kinetic fitting curve of affinity analysis, the affinity constant was calculated by analyzing the above data. The binding constant Kon value of mouse monoclonal antibody #56=$7.23 \times 10^5$/MS, the dissociation constant Kd value=$8.89 \times 10^{-6}$/s, the equilibrium dissociation constant Kd value=KD/Kon=$1.23 \times 10^{-11}$M (0.0123 nM); the binding constant Kon value of mouse monoclonal antibody #2=$1.83 \times 10^6$/MS, the dissociation constant KD Value=$2.92 \times 10^{-5}$/s, equilibrium dissociation constant Kd=KD/Kon=$1.59 \times 10^{-11}$M. The binding affinity of mouse monoclonal antibody #56 and #2 against hNGF is very high, which can reach the order of $10^{-11}$M.

Example 5. Subtype Identification and Variable Region Amplification of Anti-hNGF Mouse Monoclonal Antibody Antibody subtype identification: take the culture supernatant of hybridoma cells, and identify the antibody subtype by using the isostriptm mouse monoclonal antibody subtype identification Kit (Santa Cruz Biotechnology). The subtype of monoclonal antibody #56 was identified as IgG1 (kappa), and the subtype of monoclonal antibody #2 was identified as IgG1 (kappa).

Antibody variable region amplification: the candidate hybridoma cells A56 and A2 were cultured to a total number of $10^7$ cells. The cells were collected by centrifugation at 1000 rpm for 10 minutes. The total RNA was extracted by Trizol Kit (Invitrogen), the first strand cDNA was synthesized by smart race, and the corresponding antibody variable region DNA sequence of hybridoma cells was amplified by using the first strand cDNA as the subsequent template. According to the results of subtype identification, the heavy chain and light chain constant region sequences of the antibody subtype were obtained, and specific nested PCR primers were designed. The primer sequences used in the amplification reaction complemented the first frame region and constant region of the antibody variable region. The target gene was amplified by conventional PCR, and the amplified product was sequenced. The heavy chain variable region sequence SEQ ID No. 13 and light chain variable region sequence SEQ ID No. 14 of A56 secreting antibody were obtained. The amino acid sequence of the heavy chain CDR (CDR-H1, CDR-H2 and CDR-H3) of the antibody was identified as SEQ ID The amino acid sequences of light chain CDR (CDR-L1, CDR-L2 and CDR-L3) are shown in SEQ ID No. 7, 9 and 11, respectively. Hybridoma clone A2 secretes the heavy chain variable region sequence SEQ ID No. 15 and light chain variable region sequence SEQ ID No. 16 of antibody Chen 2; the amino acid sequence of heavy chain CDR (CDR-H1, CDR-H2 and CDR-H3) of the antibody is shown as SEQ ID No. 2, 4 and 6, and the amino acid sequence of light chain CDR (CDR-L1, CDR-L2 and CDR-L3) is shown as SEQ ID No. 8, 10 and 12, respectively. The above CDR region sequence is defined by IMgt method, and any other known CDR region sequence determination method in the art can also be used to identify the amino acid residues of CDR region in the variable region.

Example 6. Humanization of Mouse Antibody Against hNGF 6.1 Sequencing of Antibody Variable Region and Antibody Typing According to the variable region sequence of antibody secreted by hybridoma cells, the humanization of antibody was carried out by CDR transplantation. In short, the process of humanization involves the following steps: comparing the amino acid sequence of antibody secreted by hybridoma cells with that of antibody of human embryonic line to find out the sequence with high homology; analyzing and investigating HLA-DR After that, using computer simulation technology, we used molecular docking to analyze the amino acid sequence of the variable region and its surrounding framework, and investigated its three-dimensional binding mode. By calculating the electrostatic force, van der Waals force, hydrophobicity and entropy, the key amino acids which can interact with NGF and maintain the spatial framework in the amino acid sequence of antibody secreted by hybridoma cells were analyzed, and then grafted back to the selected human embryonic antibody framework.

Among them, mouse antibody #56 was constructed with human IGHV4-38-2 * 02 heavy chain variable region and human IGKV1-33 * 01 light chain variable region as template sequences, and four different humanized antibodies were constructed, namely AB5C2, ab5c3, ab5c4 and ab5c5. At the same time, a human mouse chimeric antibody AB5C1 was constructed by grafting the heavy chain variable region of mouse antibody into the heavy chain constant region of human IgG1 and the light chain variable region of mouse antibody into the light chain constant region of human kappa. The amino acid sequence of the variable region of the humanized antibody is shown in Table 1.

Among them, mouse antibody #2 was based on human IGHV1-46 * 01 heavy chain variable region and human IGKV1-n11 * 01 light chain variable region as template sequences. Four different humanized antibodies were constructed, ab5d2, ab5d3, ab5d4 and ab5d5, respectively. At the same time, a human mouse chimeric antibody ab5d1 was constructed, which was obtained by grafting the heavy chain variable region of mouse antibody into the heavy chain constant region of human IgG1 and the light chain variable region of mouse antibody into the light chain constant region of human kappa. The amino acid sequence of the variable region of the humanized antibody is shown in Table 1.

In addition, the surface remodeling method was used to humanize the variable region sequence of the antibody secreted by the hybridoma cells. The surface remodeling method refers to the humanization of the amino acid residues on the surface of heteroantibodies. It only replaces the regions with obvious differences from the surface amino acids of human antibodies. On the basis of maintaining the antibody activity and reducing the heterogeneity, it selects the amino acid replacement similar to the surface residues of human antibodies. Specifically, the process of humanization of surface remodeling involves the following steps: first, the amino acid sequence of antibody secreted by hybridoma cells is compared with that of antibody of human embryonic line to find out the sequence with high homology; then, the computer simulation technology is used to select solvent When the accessibility is more than 30%, the exposed surface amino acids will be replaced by the adult embryonic antibody amino acids. As far as possible, the residues that affect the size, charge and hydrophobicity of the side chain, or may form hydrogen bond and thus affect the conformation of the complementary determining region of the antibody should not be replaced. Among them, human antibody AB5C6 was constructed by using human IGHV4-38-2 * 02 heavy chain variable region and human IGKV1-33 * 01 light chain variable region as template sequences, and human IGHV1-46 * 01 heavy chain variable region and human IGKV1-n11 * 01 light chain variable region as template sequences. The amino acid sequence of the variable region of the humanized antibody is shown in Table 1.

The affinity of the humanized antibody obtained by the method of example 4 is shown in Table 2.

TABLE 1

Amino acid sequence of variable region of the humanized antibody

| Name | variable region of HC | variable region of LC |
| --- | --- | --- |
| AB5C2 | SEQ ID NO: 17 | SEQ ID NO: 18 |
| AB5C3 | SEQ ID NO: 19 | SEQ ID NO: 20 |
| AB5C4 | SEQ ID NO: 21 | SEQ ID NO: 22 |
| AB5C5 | SEQ ID NO: 23 | SEQ ID NO: 24 |
| AB5C6 | SEQ ID NO: 25 | SEQ ID NO: 26 |
| AB5D2 | SEQ ID NO: 27 | SEQ ID NO: 28 |
| AB5D3 | SEQ ID NO: 29 | SEQ ID NO: 30 |
| AB5D4 | SEQ ID NO: 31 | SEQ ID NO: 32 |
| AB5D5 | SEQ ID NO: 33 | SEQ ID NO: 34 |
| AB5D6 | SEQ ID NO: 35 | SEQ ID NO: 36 |

TABLE 2

Binding affinity of the humanized antibody

| 抗体 | $K_D$ (M) | kon (1/Ms) | kd (1/s) |
|---|---|---|---|
| AB5C1 | 2.99E-11 | 1.81E+06 | 5.40E-05 |
| AB5C2 | 1.30E-12 | 1.66E+06 | 2.16E-06 |
| AB5C3 | 7.55E-12 | 1.31E+06 | 9.87E-06 |
| AB5C4 | 1.53E-11 | 1.46E+06 | 2.23E-05 |
| AB5C5 | 8.90E-12 | 1.78E+06 | 1.59E-05 |
| AB5C6 | 1.02E-11 | 1.59E+06 | 1.61E-05 |
| AB5D1 | 1.06E-11 | 1.46E+06 | 1.55E-05 |
| AB5D2 | 6.33E-12 | 1.25E+06 | 7.94E-06 |
| AB5D3 | 1.29E-11 | 1.49E+06 | 1.92E-05 |
| AB5D4 | 1.82E-11 | 1.78E+06 | 3.25E-05 |
| AB5D5 | 1.54E-11 | 1.23E+06 | 1.89E-05 |
| AB5D6 | 1.57E-11 | 1.41E+06 | 2.22E-05 |

The amino acid sequences of the CDR regions of mouse McAbs #56 and #2 and their derived 10 humanized antibodies AB5C2, AB5C3, AB5C4, AB5C5, AB5C6, AB5D2, AB5D3, AB5D4, AB5D5 and AB5D6 are shown in TABLE 3-1 to TABLE 3-2, wherein the amino acid sequences of CDR are defined by Kabat and IMGT methods respectively, and the amino acid sequences of CDR region mutations in the humanized antibodies shown in TABLE 3-1and TABLE 3-2 are highlighted using underline.

TABLE 3-1

CDR amino acid sequences of the #56 NGF antibody and its derived humanized antibodies

| | | #56 | AB5C2  AB5C6 | AB5C3 | AB5C4  AB5C5 |
|---|---|---|---|---|---|
| Kabat | CDR-H1 | GYGVN (SEQ NO ID: 37) | GYGVN (SEQ NO ID: 37) | GYG<u>WG</u> (SEQ NO ID: 47) | GYG<u>WG</u> (SEQ NO ID: 47) |
| | CDR-H2 | MIWADGDTDYNSALKS (SEQ NO ID: 39) | MIWADGDTDYNSALKS (SEQ NO ID: 39) | <u>S</u>IWADGDT<u>YY</u>N<u>PSL</u>KS (SEQ NO ID: 48) | <u>S</u>IWADGDT<u>YY</u>N<u>PSL</u>KS (SEQ NO ID: 48) |
| | CDR-H3 | DSYYYGYNFFDV (SEQ NO ID: 41) | DSYYYGYNFFDV (SEQ NO ID: 41) | DSYYYGYNFFDV (SEQ NO ID: 41) | DSYYYGYNFFDV (SEQ NO ID: 41) |
| | CDR-L1 | RASQDISNYLN (SEQ NO ID: 43) | RASQDISNYLN (SEQ NO ID: 43) | <u>Q</u>ASQDISNYLN (SEQ NO ID: 49) | <u>Q</u>ASQDISNYLN (SEQ NO ID: 49) |
| | CDR-L2 | YTSRLHS (SEQ NO ID: 45) | YTSRLHS (SEQ NO ID: 45) | YTS<u>NLET</u> (SEQ NO ID: 50) | YTS<u>NLES</u> (SEQ NO ID: 51) |
| | CDR-L3 | QQGNTLPRT (SEQ NO ID: 11) | QQGNTLPRT (SEQ NO ID: 11) | QQGNTLPRT (SEQ NO ID: 11) | QQGNTLPRT (SEQ NO ID: 11) |
| IMGT | CDR-H1 | GFSLTGYG (SEQ NO ID: 1) | | | |
| | CDR-H2 | IWADGDT (SEQ NO ID: 3) | | | |
| | CDR-H3 | ARDSYYYGYNFFDV (SEQ NO ID: 5) | | | |
| | CDR-L1 | QDISNY (SEQ NO ID: 7) | | | |
| | CDR-L2 | YTS (SEQ NO ID: 9) | | | |
| | CDR-L3 | QQGNTLPRT (SEQ NO ID: 11) | | | |

TABLE 3-2

CDR amino acid sequences of the #2 NGF antibody and its derived humanized antibodies

| | | #2 | AB5D2  AB5D6 | AB5D3 | AB5D4 | AB5D5 |
|---|---|---|---|---|---|---|
| Kabat | CDR-H1 | DYWMQ (SEQ NO ID: 38) | DYWMQ (SEQ NO ID: 38) | DYWM<u>H</u> (SEQ NO ID: 52) | DYWM<u>H</u> (SEQ NO ID: 52) | DYWM<u>H</u> (SEQ NO ID: 52) |
| | CDR-H2 | TIYPGDGYTRYIQKFKG (SEQ NO ID: 40) | TIYPGDGYTRYIQKFKG (SEQ NO ID: 40) | <u>I</u>IYPGDGYT<u>S</u>YA<u>QKFQG</u> (SEQ NO ID: 53) | <u>I</u>IYPGDGYT<u>S</u>YA<u>QKFQG</u> (SEQ NO ID: 53) | <u>I</u>IYPGDGYT<u>S</u>YIQKF<u>Q</u>G (SEQ NO ID: 54) |
| | CDR-H3 | RAAYYTMDY (SEQ NO ID: 42) | RAAYYTMDY (SEQ NO ID: 42) | RAAYYTMDY (SEQ NO ID: 42) | RAAYYTMDY (SEQ NO ID: 42) | RAAYYTMDY (SEQ NO ID: 42) |
| | CDR-L1 | KASQDVNTAVA (SEQ NO ID: 44) | KASQDVNTAVA (SEQ NO ID: 44) | <u>R</u>ASQDVNTA<u>L</u>A (SEQ NO ID: 55) | <u>R</u>ASQDVNTA<u>L</u>A (SEQ NO ID: 55) | <u>R</u>ASQDVNTA<u>L</u>A (SEQ NO ID: 55) |

TABLE 3-2-continued

CDR amino acid sequences of the #2 NGF antibody and its derived humanized antibodies

|  | #2 | AB5D2 | AB5D6 | AB5D3 | AB5D4 | AB5D5 |
|---|---|---|---|---|---|---|
| CDR-L2 | WASTRHT (SEQ NO ID: 46) | WASTRHT (SEQ NO ID: 46) |  | WAS<u>RLES</u> (SEQ NO ID: 56) | WAS<u>RLET</u> (SEQ NO ID: 57) | WAS<u>RLET</u> (SEQ NO ID: 57) |
| CDR-L3 | QQHYSSPWT (SEQ NO ID: 12) | QQHYSSPWT (SEQ NO ID: 12) |  | QQHYSSPWT (SEQ NO ID: 12) | QQHYSSPWT (SEQ NO ID: 12) | QQHYSSPWT (SEQ NO ID: 12) |
| IMGT CDR-H1 |  |  |  | GYTFTDYW (SEQ NO ID: 2) |  |  |
| CDR-H2 |  |  |  | IYPGDGYT (SEQ NO ID: 4) |  |  |
| CDR-H3 |  |  |  | ARRAAYYTMDY (SEQ NO ID: 6) |  |  |
| CDR-L1 |  |  |  | QDVNTA (SEQ NO ID: 8) |  |  |
| CDR-L2 |  |  |  | WAS (SEQ NO ID: 10) |  |  |
| CDR-L3 |  |  |  | QQHYSSPWT (SEQ NO ID: 12) |  |  |

FIG. 3-1 shows the amino acid sequences of HC variable region of five humanized NGF antibodies and mouse NGF antibody #56. FIG. 3-2 shows the amino acid sequences of the LC variable region of 5 humanized antibodies and mouse antibody #56. In the variable region, CDR and framework region are labeled as listed above, and CDR of HC and LC variable region is defined by IMGT method.

FIG. 4-1 shows the amino acid sequences of HC variable region of five humanized NGF antibodies and mouse NGF antibody #2. FIG. 4-2 shows the amino acid sequences of the LC variable region of five humanized NGF antibodies and mouse NGF antibody #2. In the variable region, CDR and framework region are labeled as listed above, and CDR of HC and LC variable region is defined by IMGT method.

6.2 Expression Vector and Protein Expression of the Humanized Antibodies

The cDNA of HC and LC obtained by the above method was inserted into the pCMAB2M eukaryotic expression vector (constructed in our laboratory) to construct the humanized expression vector. The expression vector plasmid contains the early gene promoter enhancer of cytomegalovirus required for high level expression in mammalian cells. At the same time, the vector plasmids contain selection marker genes with ampicillin resistance in bacteria and G418 resistance in mammalian cells. In addition, the vector plasmid contains dihydrofolate reductase (DHFR) gene, which can co amplify antibody gene and DHFR gene with methotrexate (MTX) in suitable host cells.

The constructed recombinant expression vector plasmid was transfected into mammalian host cell line to express humanized antibody. In order to stabilize the high level of expression, the preferred host cell line is DHFR-deficient Chinese hamster ovary (CHO) cells (see U.S. Pat. No. 4,818,679). The preferred transfection method is electroporation, while other transfection methods can also be used, including calcium phosphate co-deposition, lipid transfection and protoplast fusion. In electroporation experiment, gene pulser (bio-rad laboratories) with 250 V electric field and 960 µFD capacitance was used. $2 \times 10^7$ cells were added into the cuvette and suspended in 0.8 ml PBS, and 10 µg expression vector plasmid was linearized with pvui (Takara). 2 days after transfection, 0.2 mg/ml G418 and 200 nm MTX (sigma) were added into the cell culture medium. In order to achieve a high level of antibody expression, the transfected antibody gene was co-transfected with DHFR gene which can be inhibited by MTX. Clones were selected by limited dilution method and the activity of the clones were validated by ELISA method. After several rounds of selection and validation, the clone with high level of antibody expression was selected out. The cell culture medium of the clones were collected for determination of their biological activity in vitro and in vivo.

Example 7. Determination of Neutralization Activity of NGF Antibody In Vitro

The biological activity of NGF antibody was validated by measurement of the capability of the NGF antibody to inhibit the NGF-dependent proliferation of TF-1 cells. TF-1 cell proliferation highly dependents on granulocyte macrophage colony stimulating factor (GM-CSF). The binding of NGF to its receptor on TF-1 cell surface will induce the proliferation of TF-1 cells. Firstly, sample plates were set as 50 µl of RPMI 1640 medium containing 10% fetal bovine serum (FBS) plus 50 µl of antibodies of different concentrations and 50 µl of 800 ng/ml hNGF per well. Wells without addition of hNGF were used as negative control and medium-only wells were used as blank control. After shaking at room temperature for 30 minutes, add 100 µl $10^5$/ml TF-1 cells into each well of the sample plates, and culture the plates in a 5% CO2 incubator at 37° C. for 5-6 days. After that, 20 µl of MTT (2.5 mg/ml) was added into each well and incubated for 4 hours, and then 100 µL 10% SDS was added into each well and incubated overnight. The proliferation of the TF-1 cells was measured by monitoring the fluorescence signal at Ex570 nm and Em620 nm. Three replicates were set for each treatment, and the experiments were repeat twice for confirmation.

The results are shown in FIG. 5. Among the test groups, the binding affinity of the anti-hNGF antibody to NGF is relatively low at the concentration range from 0.005 to 0.3 µg/ml. When the concentration is higher than 0.3 µg/ml, NGF antibody showed inhibition of the effect of NGF on TF-1 cell proliferation, indicating that NGF antibody can antagonize the function of NGF. In addition, the binding affinity of NGF humanized antibody AB5C2, AB5C6 and mouse monoclonal antibody #56 are better than that of chimeric antibody AB5C1.

Example 8. In Vivo Analgesic Efficacy Study of NGF Antibodies 8.1 Efficacy Study with Post-Surgical Pain Model We used the mimic post-surgical pain mouse model to evaluate the efficacy of treatment of NGF antibodies. In this experiment, the flexor muscles of the paw of the mice were used for surgical operation with a scalpel. This surgical operation results the stimulation and finally the thermal hyperalgesia of the mice. Efficacy of NGF antibodies on the pain elimination.

SPF grade C57BL/6J male mice (Shanghai slake experimental animal Co., Ltd.) of weight around 25 g, were randomly divided into two groups with 10 mice in each group. Before the experiment, the animals were put into the Hargreaves device (type 336, IITC Life Science) for adaptation for a period of time. The environment of the adaptation is light intensity 17%, and the light cut-off time was 25 s. Before administration, the basic thermal pain threshold (the time from the beginning of strong light radiation to the occurrence of foot contraction reaction, i.e., the time of thermal pain reaction) of each mouse was measured at 0.5-2 h interval, three times in total. the average value was set as the baseline (t0 value). Before the surgical operation, NGF antibody AB5C1 was injected subcutaneously at the dose of 10 mg/kg in the test group and PBS buffer at the same volume dose (10 ml/kg) in the model group. One hour later, the flexor muscle of the right paw of the mice was separated and cut vertically. Then the site of the surgical operation was sutured. During the recovery time period, the mice were used to validate their thermal pain threshold after 1, 24, 48, 72 and 96 h of the surgical operation. The percentage of the increase of the thermal pain threshold was calculated according to the following formula: the percentage of the increase of the thermal pain threshold=(the average thermal pain threshold after administration− the average thermal pain threshold before administration)/the average thermal pain threshold before administration×100%. Statistical analysis was carried out based on the data. The experimental data was expressed by means±SD. If the data were in accordance with normal distribution, SPSS 18.0 software, one-way ANOVA or t-test was used; paired t-test was used for different influencing factors before and after treatment; nonparametric test, Mann Whitney test or Kruskal Wallis test were used for scoring statistics, $P \leq 0.05$ had significant difference, $P \leq 0$ There is a very significant difference.

Figure 6:
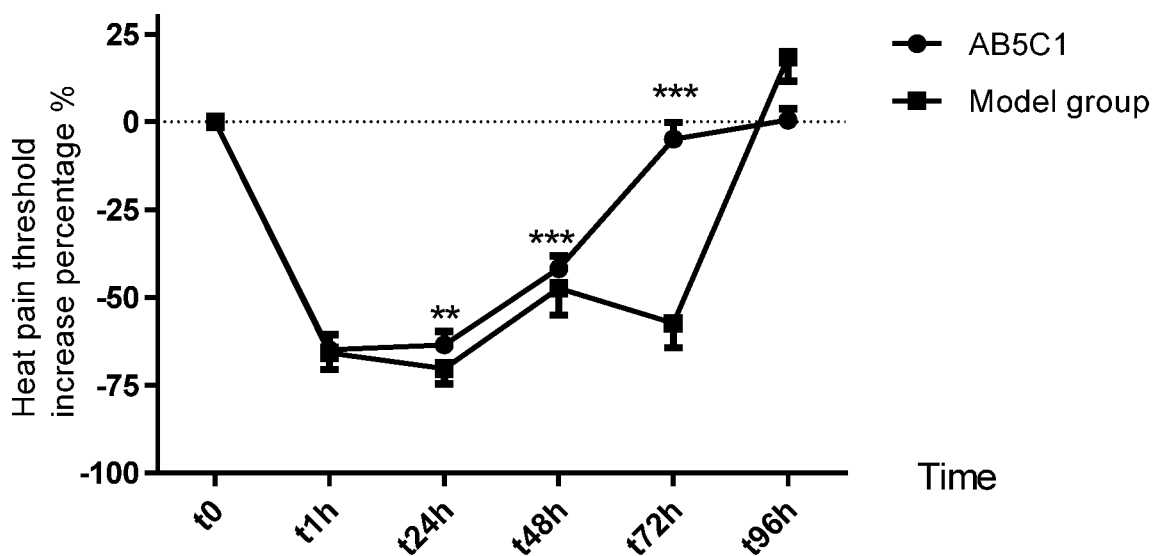

It can be seen from FIG. 6 that 1 h after the surgical operation, the thermal pain threshold of the mice in each group decreased due to post-surgical pain, while with the extension of time, the difference of the thermal pain threshold between the tested group and the model group is more and more significant. According to the student's t-test test, the time period from t24 h to 72 h is statistically significant, which shows that compared with the model group, the pre-treatment of the tested NGF antibody AB5C1 significantly reduces the post-osurgical pain. At t72 h, the threshold of thermal pain in the tested group was restored to the initial value, while that in the model group was still at a lower value; at t96 h, both groups were restored to the initial value.

8.2 Efficacy Study of NGF Antibodies with Sciatic Nerve Ligation Model

We used sciatic nerve ligation model to evaluate the effect of NGF antibody on chronic pain. SPF C57BL/6J female mice with weight of about 25 g were randomly divided into 3 groups, 5 mice in each group. Before the experiment, the test animals were put into the Hargreaves device (parameter setting as 8.1) for environment adaptation. The foot base pain threshold of each mouse of rest time was measured at 0.5-2 h interval, three times in total, and set the average value of the foot base pain threshold as the baseline (d0 value).

⅓ ~½ of the sciatic nerve in the fascia and muscle of the right femur of the mice were ligated with 7-0 silk thread. Sew layer by layer the wounds of the tested mice. In the negative control group, the sciatic nerve was not ligated. On the 10th day (d10) and 17th day (d17) after operation, NGF antibody AB5C1 was subcutaneously injected into the tested group at a dose of 100 mg/kg, and PBS buffer of equal volume (20 ml/kg) was injected into the negative control group and the model group, respectively. The thermal pain thresholds of d10, d17 before administration and d12, d14, d16, d18, d20, d21 and d23 after administration were measured, and the percentage (%) of the increase of thermal pain threshold was calculated, the formula was the same as 8.1. For statistical analysis of data, the software and analysis method are the same as 8.1

From the data in Table 4, it can be seen that on the 10th day after ligation, the thermal pain threshold of each group showed a downward trend compared with the basic thermal pain threshold measured before the experiment, and the percentage of increase of the thermal pain threshold of NGF antibody AB5C1 group, model group and negative control group was −56.31%±6.98%, −50.99%±8.19% and −20.42%±5.35%, respectively. The first two groups and negative control group were statistically analyzed by t-test, and P=0.014<0.05. After subcutaneous administration for 48 hours (d12) on the 10th day, it was found that the increase rate of NGF antibody AB5C1 in the administration group was −23.65%±5.17%, which was equivalent to that in the negative control group (−18.70%±5.98%), the mean value was much higher than that in the model group (−51.44%±1.28%), and the statistical significance was not very significant, indicating that the tested antibody showed better analgesic effect at 48 h than that of the control group. While the thermal pain threshold showed a downward trend on the 4th-7th day (d14-d17) after administration, as shown in FIG. 7. The percentage of the increase of the thermal pain threshold on the 7th day was almost the same as that of the model group, indicating that the NGF antibody was constantly metabolized and degraded in mice with the extension of time.

One week after first administration, the second administration was carried out on d17. It was observed that at 24 h (d18) and 72 h (d20) after the second administration, the increase percentage of the thermal pain threshold in NGF antibody AB5C1 group was significantly higher than that of the model group. The data are shown in Table 3, and the statistical differences are significant. Based on the data, it is speculated that there are statistical differences in 48 h treatment group, and those indirectly validated the data of the first administration. All of those during 0-72 h after administration.

TABLE 4 thermal pain threshold of mice

| Days after surgical operation (d) | AB5C1 group SD±SEM | Model group SD±SEM | Negative control group SD±SEM |
|---|---|---|---|
| d0 | 0.00% ± 0.00% | 0.00% ± 0.00% | 0.00% ± 0.00% |
| d10/before administration | −56.31% ± 6.98% | −50.99% ± 8.19% | −20.42% ± 5.35% |
| d12 | −23.65% ± 5.17% | −51.44% ± 1.28% | −18.70% ± 5.98% |
| d14 | −33.76% ± 7.43% | −32.23% ± 7.93% | −11.93% ± 5.13% |
| d16 | −33.36% ± 5.58% | −45.41% ± 3.46% | −17.46% ± 6.53% |
| d17/before administration | −42.23% ± 2.14% | −40.84% ± 4.14% | −37.29% ± 4.86% |
| d18 | −16.18% ± 5.09% | −37.35% ± 2.84% | −35.19% ± 4.26% |
| d20 | −27.62% ± 3.55% | −38.76% ± 3.01% | −20.69% ± 6.34% |
| d21 | −31.58% ± 3.62% | −37.25% ± 4.23% | −17.91% ± 3.79% |
| d23 | −40.86% ± 3.22% | −39.25% ± 2.44% | −25.32% ± 3.00% |

8.3 Efficacy Study of NGF Antibodies with Gouty Arthritis Mice Model Induced by Sodium Urate This experiment is to validate the efficacy of NGF antibody on mice acute gouty arthritis models which induced by sodium urate. SPF C57BL/6J female mice with weight of about 25 g were randomly divided into 3 groups, 8 mice in each group. Before the experiment, the mice were put into the Hargreaves device (parameter setting as 8.1) to adapt for a period of time. The foot base pain threshold of each mouse of rest time was measured at 0.5-2 h interval, three times in total, and set the average value of the foot base pain threshold as the baseline (d0 value). NGF antibody AB5C1 and AB5C2 were injected subcutaneously at the dose of 10 mg/kg in the tested group, and PBS buffer of equal volume (10 ml/kg) was injected in the model group. One hour after administration, 2.5% sodium urate (sigma) solution was injected into the ankle joint for 30 μL; the post foot thermal pain threshold was measured at 4, 24 and 48 h after injection of sodium urate at 0.5-2 h interval, three times in total. The average value was taken as the actual threshold value, and the percentage (%) of increase in the thermal pain threshold was calculated using the same formula as 8.1. For statistical analysis of data, the software and analysis method are the same as 8.1.

FIG. 8 showed that at 4-6 h after administration, the NGF antibody AB5C1 and AB5C2 significantly prolonged the thermal pain threshold of mice in gouty arthritis mice model. At 4-6 h, 24 h and 48 h, the statistical difference of AB5C1 was very significant, while the statistical difference of NGF antibody AB5C2 group was only significant at the day of administration; however, the mean value of the two groups was still very high compared with the model group, showing significantly prolonged the thermal pain threshold of mice.

8.4 Efficacy Study of NGF Antibodies with Inflammatory Pain Model Induced by Freund's Adjuvant To validate if the NGF antibodies could alleviate the pain in chronic peripheral inflammatory mice model or not, C57BL/6J mice after subcutaneous injection of Freund's adjuvant were used as test model. SPF C57BL/6J female mice with weight of about 25 g were randomly divided into 3 groups, 8 mice in each group. Before the experiment, the mice were put into the Hargreaves device (parameter setting as 8.1) to adapt for a period of time. The foot base pain threshold of each mouse of rest time was measured at 0.5-2 h interval, three times in total, and set the average value of the foot base pain threshold as the baseline (d0 value). NGF antibody AB5C1 and AB5C6 were injected subcutaneously at the dose of 10 mg/kg in the tested group, and PBS buffer of equal volume (10 ml/kg) was injected into the model group. After one hour of administration, 50 μl of 0.5% complete Freund's adjuvant (BD company) solution was injected into the ankle joint; after 4, 24, 48, 72 and 96 hours of injection, the thermal pain threshold of the foot bottom of the hind limbs of each mouse was measured at 0.5-2 h interval, three times in total. The average value was taken as the actual threshold value, and the increase percentage (%) of the thermal pain threshold was calculated according to the formula listed in 8.1. For statistical analysis of data, the software and analysis method are the same as 8.1.

FIG. 9 shows that 4-72 h after administration, the thermal pain threshold of NGF antibody AB5C6 group is higher than that of the model group and the NGF antibody AB5C1 group, and the statistical difference is significant. The efficacy of NGF antibody AB5C1 is slightly weaker than that of NGF antibody AB5C6, and the statistical difference can only be significant at 48 h after administration. There was no significant difference between them after 96 hours of administration. In conclusion, the tested NGF antibody can relieve pain cause by immune inflammatory in the pain mice model, and among them, NGF antibody AB5C6 showed better efficacy than that of NGF antibody AB5C1.

It is understood that the examples and embodiments described herein are for illustrative purpose only and that various modifications or changes in light thereof will be suggested to persons skilled in the art and are to be included within the spirit and purview of this application. Although preferred examples of the invention are described, it is to be understood that those skilled in the art may make various changes in accordance with the teachings herein, which are not contrary to the scope of the invention.

All references mentioned in the invention are cited as references in the application, just as each reference is cited as a reference separately. In addition, it should be understood that after reading the above teaching contents of the invention, those skilled in the art can make various changes or modifications to the invention, and these equivalent forms also fall within the scope of the claims attached to the application.

The invention claimed is:

1. An antibody or an antigen binding fragment thereof, which binds to human nerve growth factor, comprises:
   a heavy chain variable region, which comprises CDR-H1, CDR-H2, and CDR-H3; and
   a light chain variable region, which comprises CDR-L1, CDR-L2 and CDR-L3 wherein: said CDR-H1 comprises an amino acid sequence as shown in SEQ ID NO: 1, said CDR-H2 comprises an amino acid sequence as shown in SEQ ID NO: 3, said CDR-H3 comprises an amino acid sequence as shown in SEQ ID NO: 5, said CDR-L1 comprises an amino acid sequence as shown in SEQ ID NO: 7, said CDR-L2 comprises an amino acid sequence having Tyr-Thr-Ser (Tyrosine— Threonine— Serine), and said CDR-L3 comprises an amino acid sequence as shown in SEQ ID NO: 11.

2. The antibody or its antigen binding fragment according to claim 1, which is characterized in that the antibody or its antigen binding fragment is mouse derived, chimeric or humanized.

3. The antibody or its antigen binding fragment according to claim 2, which is characterized in that if the antibody or its antigen binding fragment is mouse derived or chimeric, its heavy chain variable region further comprises the heavy chain fr region of mouse IgG1, IgG2a, IgG2b, IgG3 or its variants; and its light chain variable region comprises the light chain fr region of mouse κ, λ chain or its variants.

4. The antibody or its antigen binding fragment according to claim 1, which is characterized in that it comprises a heavy chain variable region and a light chain variable region, and the heavy chain variable area is shown in SEQ ID No. 25, and the light chain variable area is shown in SEQ ID No. 26.

5. The antibody or its antigen binding fragment according to claim 1, which is characterized in that the antibody or its antigen binding fragment is a full-length antibody further containing the antibody constant region of human or mouse, or only containing the antigen binding fragment of fab, Fab ', f (ab') 2 or scFv.

6. The antibody or its antigen binding fragment according to claim 1, wherein the Kd value of the antibody or its antigen binding fragment binding to NGF (Nerve Growth Factor) is $5\times10^{-11}$ M or below.

7. A pharmaceutical composition, characterized in that the composition comprises the antibody or the antigen binding fragment of claim 1, as well as a pharmaceutically acceptable carrier, excipient or diluent.

8. The antibody or its antigen binding fragment according to claim 1, wherein the Kd value of the antibody or its antigen binding fragment binding to NGF (Nerve Growth Factor) is $1\times10^{-11}$ M or below.

* * * * *